United States Patent
Taylor et al.

(10) Patent No.: US 9,308,047 B2
(45) Date of Patent: *Apr. 12, 2016

(54) RAPID EXCHANGE BIAS LASER CATHETER DESIGN

(71) Applicant: The Spectranetics Corporation, Colorado Springs, CO (US)

(72) Inventors: Kevin D. Taylor, Colorado Springs, CO (US); Wade Bowe, Colorado Springs, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 176 days.

This patent is subject to a terminal disclaimer.

(21) Appl. No.: 14/137,424

(22) Filed: Dec. 20, 2013

(65) Prior Publication Data

US 2014/0114298 A1    Apr. 24, 2014

Related U.S. Application Data

(63) Continuation of application No. 12/337,232, filed on Dec. 17, 2008, now Pat. No. 8,628,519, which is a continuation-in-part of application No. 11/228,845, filed on Sep. 16, 2005, now Pat. No. 7,572,254.

(60) Provisional application No. 60/611,191, filed on Sep. 17, 2004.

(51) Int. Cl.
*A61B 18/24* (2006.01)
*A61B 17/22* (2006.01)
*A61B 18/22* (2006.01)

(52) U.S. Cl.
CPC ............... *A61B 18/245* (2013.01); *A61B 18/24* (2013.01); *A61B 2017/22038* (2013.01); *A61B 2017/22061* (2013.01); *A61B 2018/2238* (2013.01)

(58) Field of Classification Search
CPC ............................ A61B 18/20; A61B 2018/20
See application file for complete search history.

(56) References Cited

U.S. PATENT DOCUMENTS

| 4,053,845 A | 10/1977 | Gould |
| 4,641,912 A | 2/1987 | Goldenberg |

(Continued)

FOREIGN PATENT DOCUMENTS

| GB | 2208807 | 4/1989 |
| WO | WO 98/19614 | 5/1998 |

OTHER PUBLICATIONS

U.S. Appl. No. 13/968,993, filed Aug. 16, 2013, Taylor et al.

(Continued)

*Primary Examiner* — Lynsey Crandall
(74) *Attorney, Agent, or Firm* — Faegre Baker Daniels LLP

(57) ABSTRACT

Embodiments of a balloon biasing laser catheter are provided. In some embodiments, the laser catheter may include a distal tip that extends from the distal end of the catheter from a point near the light guide aperture. The distal tip may be disposed at the periphery of the catheter. In some embodiments, a balloon may be disposed between the light guide aperture and the distal tip, such that the a light guide extending from the aperture may be disposed proximate with the distal tip having the balloon in between. A retaining wire may be coupled with the distal tip and slidably coupled with the light guide. The retaining wire may keep the light guide biased relatively parallel with the distal tip and/or the catheter body when the balloon is inflated. The light guide may include a guidewire lumen the extends to the distal end of the distal tip.

20 Claims, 17 Drawing Sheets

(56) References Cited

U.S. PATENT DOCUMENTS

| | | |
|---|---|---|
| 4,669,465 A | 6/1987 | Moore et al. |
| 4,686,979 A | 8/1987 | Gruen et al. |
| 4,732,448 A | 3/1988 | Goldenberg |
| 4,747,405 A | 5/1988 | Leckrone |
| 4,769,005 A | 9/1988 | Ginsburg et al. |
| 4,784,132 A | 11/1988 | Fox et al. |
| 4,788,975 A | 12/1988 | Shturman et al. |
| 4,799,754 A | 1/1989 | Goldenberg |
| 4,807,620 A | 2/1989 | Strul et al. |
| 4,830,460 A | 5/1989 | Goldenberg |
| 4,844,062 A | 7/1989 | Wells |
| 4,848,336 A | 7/1989 | Fox et al. |
| 4,924,863 A | 5/1990 | Sterzer |
| 5,016,964 A | 5/1991 | Donnelly |
| 5,024,234 A | 6/1991 | Leary et al. |
| 5,026,366 A | 6/1991 | Leckrone |
| 5,040,548 A | 8/1991 | Yock |
| 5,041,108 A | 8/1991 | Fox et al. |
| 5,176,674 A * | 1/1993 | Hofmann .................. 606/7 |
| 5,188,632 A | 2/1993 | Goldenberg |
| 5,207,672 A | 5/1993 | Roth et al. |
| 5,217,454 A | 6/1993 | Khoury |
| 5,250,045 A | 10/1993 | Bohley |
| 5,263,953 A | 11/1993 | Bagby |
| 5,267,341 A | 11/1993 | Shearin |
| 5,300,085 A | 4/1994 | Yock |
| 5,304,171 A | 4/1994 | Gregory et al. |
| 5,318,032 A | 6/1994 | Lonsbury et al. |
| 5,350,375 A | 9/1994 | Deckelbaum et al. |
| 5,350,377 A | 9/1994 | Winston et al. |
| 5,350,395 A | 9/1994 | Yock |
| 5,352,197 A | 10/1994 | Hammersmark et al. |
| 5,377,683 A | 1/1995 | Barken |
| 5,395,361 A * | 3/1995 | Fox et al. .................. 606/15 |
| 5,415,653 A | 5/1995 | Wardle et al. |
| 5,425,355 A | 6/1995 | Kulick |
| 5,429,604 A | 7/1995 | Hammersmark et al. |
| 5,429,617 A | 7/1995 | Hammersmark et al. |
| 5,440,664 A | 8/1995 | Harrington et al. |
| 5,451,233 A | 9/1995 | Yock |
| 5,456,680 A | 10/1995 | Taylor et al. |
| 5,464,395 A | 11/1995 | Faxon et al. |
| 5,470,330 A | 11/1995 | Goldenberg et al. |
| 5,484,433 A | 1/1996 | Taylor et al. |
| 5,514,128 A | 5/1996 | Hillsman et al. |
| 5,571,151 A | 11/1996 | Gregory |
| 5,573,531 A | 11/1996 | Gregory |
| 5,623,940 A | 4/1997 | Daikuzono |
| 5,643,251 A | 7/1997 | Hillsman et al. |
| 5,649,923 A | 7/1997 | Gregory et al. |
| 5,657,760 A | 8/1997 | Ying et al. |
| 5,722,972 A | 3/1998 | Power et al. |
| 5,755,714 A | 5/1998 | Murphy-Chutorian |
| 5,792,118 A | 8/1998 | Kurth et al. |
| 5,803,083 A | 9/1998 | Buck et al. |
| 5,817,144 A | 10/1998 | Gregory |
| 5,824,026 A | 10/1998 | Diaz |
| 5,836,946 A | 11/1998 | Diaz et al. |
| RE36,104 E | 2/1999 | Solar |
| 5,891,133 A | 4/1999 | Murphy-Chutorian |
| 5,938,609 A | 8/1999 | Pomeranz |
| 5,976,124 A | 11/1999 | Reiser |
| 5,989,243 A | 11/1999 | Goldenberg |
| 6,022,342 A | 2/2000 | Mukherjee |
| 6,033,402 A | 3/2000 | Tu et al. |
| 6,036,715 A | 3/2000 | Yock |
| 6,056,743 A | 5/2000 | Ellis et al. |
| 6,066,130 A | 5/2000 | Gregory et al. |
| 6,117,128 A | 9/2000 | Gregory |
| 6,231,563 B1 | 5/2001 | White et al. |
| 6,287,297 B1 | 9/2001 | Woodruff et al. |
| 6,290,668 B1 | 9/2001 | Gregory et al. |
| 6,302,875 B1 | 10/2001 | Makower et al. |
| 6,419,684 B1 | 7/2002 | Heisler et al. |
| 6,432,115 B1 | 8/2002 | Mollenauer et al. |
| 6,447,504 B1 | 9/2002 | Ben-Haim et al. |
| 6,447,525 B2 | 9/2002 | Follmer et al. |
| 6,458,098 B1 | 10/2002 | Kanesaka |
| 6,575,993 B1 | 6/2003 | Yock |
| 6,743,208 B1 | 6/2004 | Coyle |
| 7,238,178 B2 | 7/2007 | Maschke |
| 7,572,254 B2 | 8/2009 | Hebert et al. |
| 7,846,153 B2 | 12/2010 | Hebert et al. |
| 8,016,748 B2 | 9/2011 | Mourlas et al. |
| 8,545,488 B2 | 10/2013 | Taylor et al. |
| 8,628,519 B2 | 1/2014 | Taylor et al. |
| 2001/0014805 A1 | 8/2001 | Burbank et al. |
| 2002/0045811 A1 | 4/2002 | Kittrell et al. |
| 2002/0103459 A1 | 8/2002 | Sparks et al. |
| 2003/0032936 A1 | 2/2003 | Lederman |
| 2003/0078566 A1 | 4/2003 | Elliott et al. |
| 2003/0219202 A1 | 11/2003 | Loeb et al. |
| 2004/0059280 A1 | 3/2004 | Makower et al. |
| 2004/0133154 A1 | 7/2004 | Flaherty et al. |
| 2004/0162548 A1 | 8/2004 | Reiser |
| 2005/0149176 A1 | 7/2005 | Heggestuen et al. |
| 2006/0094930 A1 | 5/2006 | Sparks et al. |
| 2008/0108867 A1 | 5/2008 | Zhou |
| 2010/0114081 A1 | 5/2010 | Keeler et al. |
| 2010/0152717 A1 | 6/2010 | Keeler |

OTHER PUBLICATIONS

Grundfest et al., "Laser Ablation of Human Atherosclerotic Plaque Without Adjacent Tissue Injury," JACC vol. 5, No. 4, pp. 929-933, Apr. 1985.

International Search Report for International (PCT) Patent Application No. PCT/US05/33029, mailed Oct. 3, 2006, 1 page, 1 page.

Extended European Search Report for European Patent Application No. 05796879.4, dated Mar. 6, 2008, 7 pages, 7 pages.

Extended European Search Report for European Patent Application No. 08010688.3, dated Feb. 17, 2009, 6 pages, 6 pages.

PCT International Search Report and Written Opinion for International Application No. PCT/US2009/066133, mailed Jan. 26, 2010, 8 pages.

International Preliminary Report on Patentability for International (PCT) Patent Application No. PCT/US2009/066133, mailed Jun. 21, 2011, 8 pages, 7 pages.

Official Action for U.S. Appl. No. 11/228,845, mailed Sep. 3, 2008, 10 pages.

Official Action for U.S. Appl. No. 11/228,845, mailed Jan. 12, 2009, 13 pages.

Notice of Allowance for U.S. Appl. No. 11/228,845, mailed Jun. 5, 2009, 8 pages.

Notice of Allowance for U.S. Appl. No. 12/406,807, mailed Aug. 2, 2010, 7 pages.

Official Action for U.S. Appl. No. 12/337,232, mailed Mar. 23, 2012 Restriction Requirement, 9 pages.

Official Action for U.S. Appl. No. 12/337,232, mailed Sep. 13, 2012 10 pages.

Final Action for U.S. Appl. No. 12/337,232, mailed Apr. 23, 2013 11 pages.

Advisory Action for U.S. Appl. No. 12/337,232, mailed Aug. 8, 2013 3 pages.

Notice of Allowance for U.S. Appl. No. 12/337,232, mailed Sep. 6, 2013 11 pages.

Official Action for U.S. Appl. No. 12/649,759, mailed Jul. 16, 2012 9 pages Restriction Requirement.

Official Action for U.S. Appl. No. 12/649,759, mailed Aug. 30, 2012 11 pages.

Notice of Allowance for U.S. Appl. No. 12/649,759, mailed May 16, 2013 12 pages.

* cited by examiner

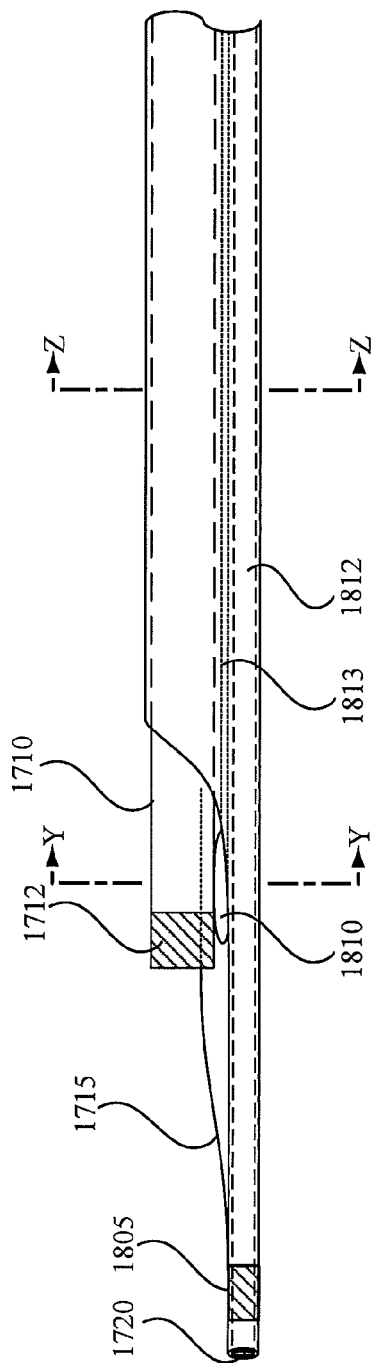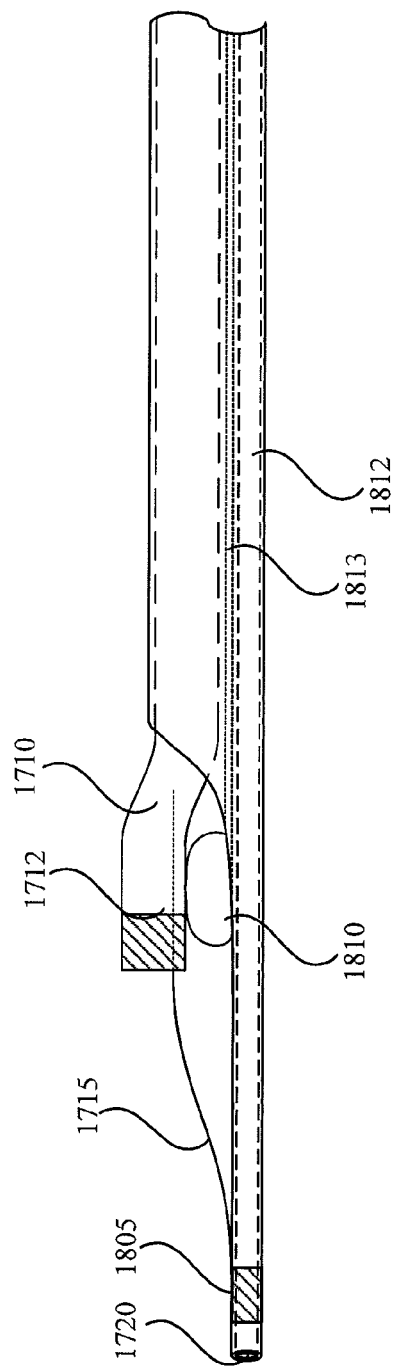

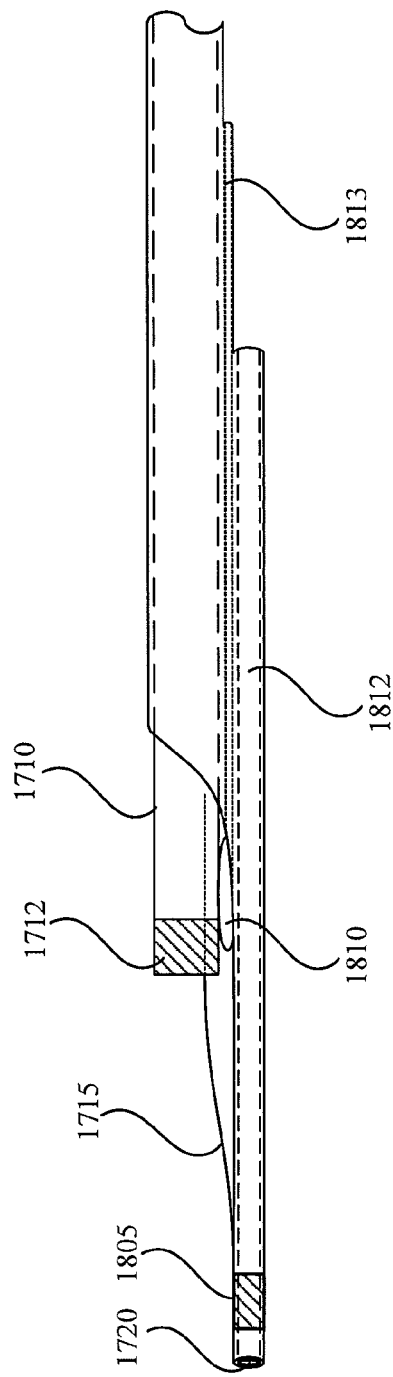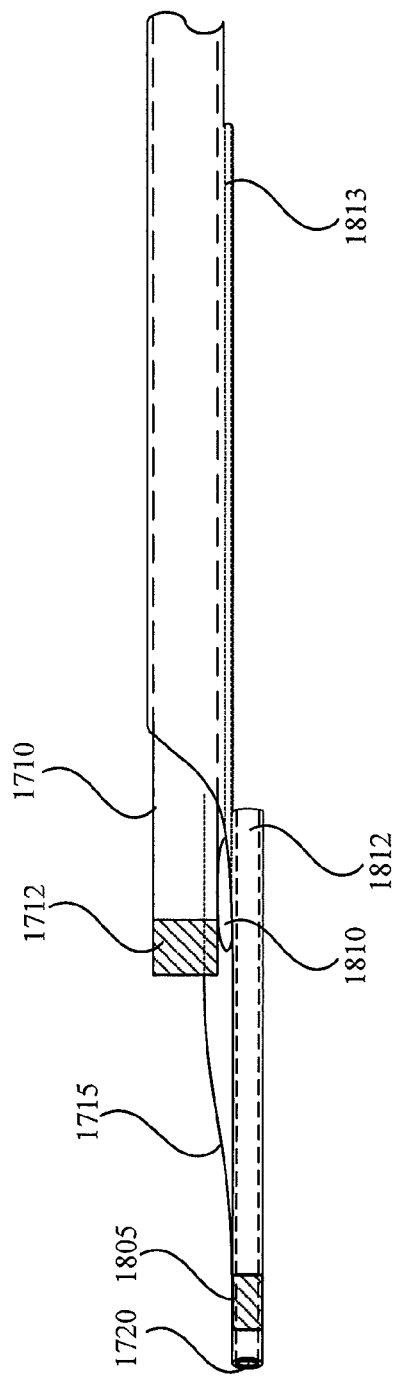

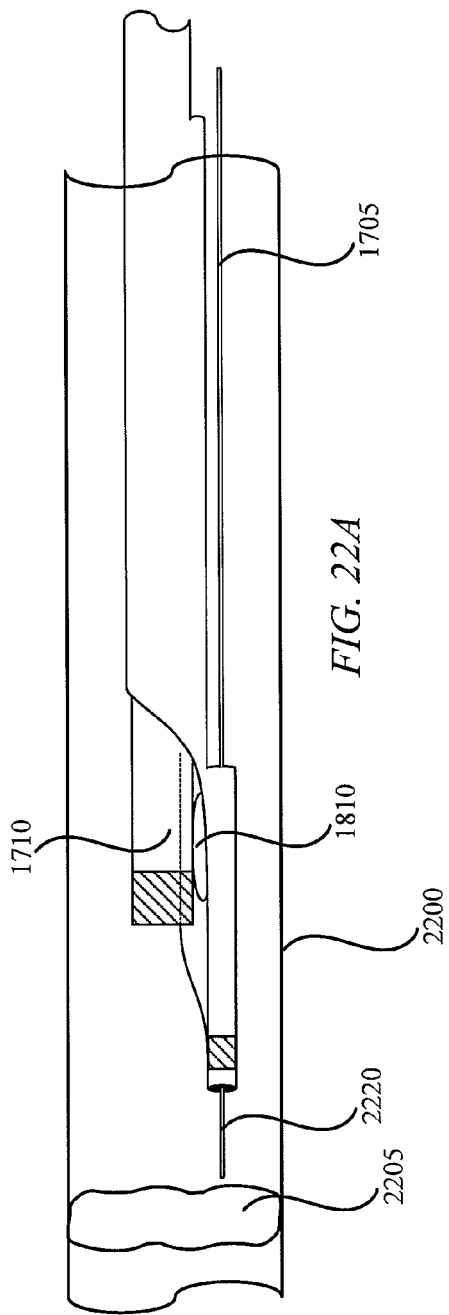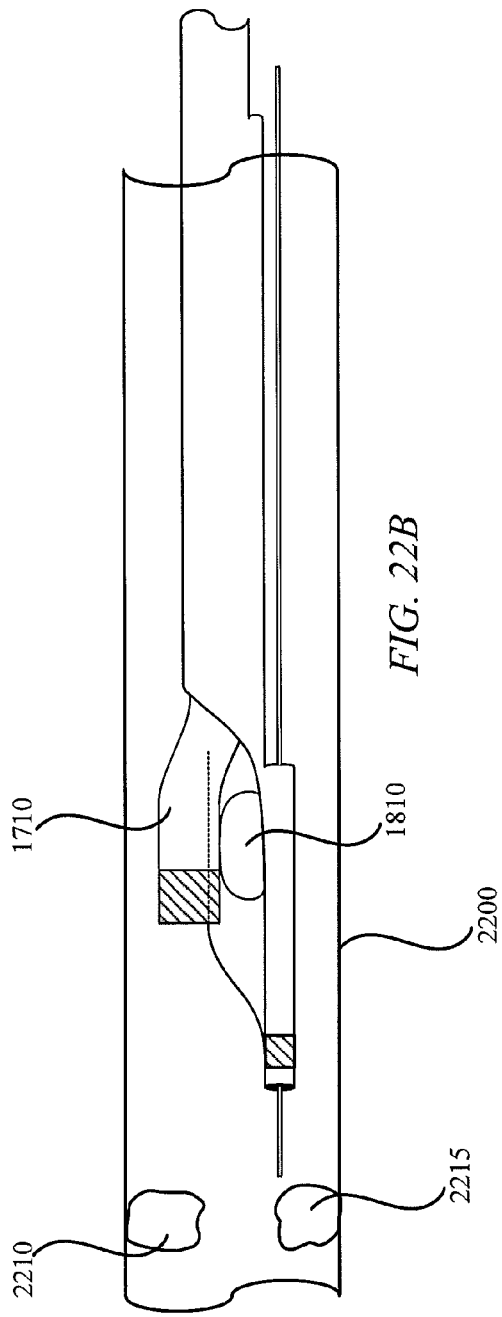

RAPID EXCHANGE BIAS LASER CATHETER DESIGN

CROSS-REFERENCES TO RELATED APPLICATIONS

This application is a continuation in part of U.S. Non-Provisional application Ser. No. 11/228,845 filed on Sep. 16, 2006, which claims the benefit of U.S. Provisional Application Ser. No. 60/611,191 filed Sep. 17, 2004, which is hereby incorporated by reference in its entirety.

TECHNICAL FIELD

The embodiments described herein are generally directed to improved apparatus and methods for the delivery of laser energy, including without limitation, to a laser delivery catheter.

BACKGROUND OF THE INVENTION

Arteries are the primary blood vessels that are responsible for providing blood and oxygen to the heart muscle. Arterial disease occurs when arteries become narrowed or blocked by a buildup of plaque (as some examples, atherosclerotic plaque or other deposits). When the blockage is severe, the flow of blood and oxygen to the heart muscle is reduced, causing chest pain. Arterial blockage by clots formed in a human body may be relieved in a number of traditional ways. Drug therapy, including nitrates, beta-blockers, and peripheral vasodilatator drugs to dilate the arteries or thrombolytic drugs to dissolve the clot, can be effective. If drug treatment fails, angioplasty may be used to reform or remove the atherosclerotic plaque or other deposits in the artery.

Traditional balloon angioplasty is sometimes used to address the blockage by inserting a narrow, flexible tube having a balloon into an artery in the arm or leg. The blocked area in the artery can be stretched apart by passing the balloon to the desired treatment site and gently inflating it a certain degree. In the event drug therapy is ineffective or angioplasty is ineffective or too risky (often introduction of a balloon in an occluded artery can cause portions of the atherosclerotic material to become dislodged which may cause a total blockage at a point downstream of the subject occlusion thereby requiring emergency procedures), the procedure known as excimer laser angioplasty may be indicated.

Excimer laser angioplasty procedure is similar in some respects to conventional coronary balloon angioplasty. A narrow, flexible tube, the laser catheter, is inserted into an artery in the arm or leg. The laser catheter contains one or more optical fibers, which can transmit laser energy. The laser catheter is then advanced inside the artery to the targeted obstruction at the desired treatment site. After the laser catheter has been positioned, the laser is energized to "remove" the obstruction.

In many procedures, the lesion is often engaged similar to conventional balloon angioplasty by crossing the blockage with a guidewire. The laser catheter's thin, flexible optical fibers facilitate the desired positioning and alignment of the catheter. Using the excimer laser, the clinician performs a controlled blockage removal by sending bursts of ultraviolet light through the catheter and against the blockage, a process called "ablation." The catheter is then slowly advanced through the blockage reopening the artery. If there are multiple blockages, the catheter is advanced to the next blockage site and the above step is repeated. When the indicated blockages appear to be cleared, the catheter is withdrawn.

However, due to the configuration of the optical fibers in most prior art laser catheters, the clinician is able to ablate only material that is typically directly in front of the distal end of the catheter. Thus, the debulked tissue area is limited to an area approximately the size of the optical fiber area at the distal end of the catheter. Typically, follow-up balloon angioplasty is recommended.

Thus, it would be desirable to provide an apparatus and methods that could bias the distal end of the laser catheter in a desired direction to enable the clinician to ablate an area larger than the area of the distal end of the catheter. Furthermore, because plaque may be eccentric in a blood vessel and require directional control to adequately ablate the target area, it would be advantageous to provide an apparatus that is sufficiently flexible to travel and rotate around the target area so that the clinician may control the area to be ablated.

BRIEF SUMMARY OF THE INVENTION

A catheter comprising a catheter body, a light guide, a distal tip, a retaining wire and a balloon is provided according to one embodiment. The catheter body, for example may include a central axis, a first proximal end and a first distal end. The catheter body may also include a lumen disposed between the first proximal end and the first distal end, the lumen having an opening at the first distal end. The light guide may include a second proximal end and a second distal end. In some embodiments, the light guide may also include at least one optical fiber and may at least partially be disposed within the lumen and movable therein. The distal tip may be positioned at the periphery of the catheter body and extend from the first distal end of the catheter body. The distal tip may also include a guidewire lumen that includes a guidewire port at the distal end of the distal tip. The retaining wire may be coupled with the distal tip and slidably coupled with the light guide. The balloon, for example, may be positioned between the opening at the first distal end of the catheter body and the distal tip.

In some embodiments, the balloon may be configured to bias the light guide away from the central axis from the catheter body when the balloon is inflated. In some embodiments, the catheter may include a guidewire lumen. In some embodiments, at least a portion of the guidewire lumen may be located within the distal tip and/or a portion may be located within the catheter body. In some embodiments, the guidewire lumen may be parallel with the lumen within the catheter body. In some embodiments, the catheter body may include a proximal guidewire port and/or a distal guidewire port. In some embodiments, the catheter may also include a balloon and/or a balloon lumen (or tube) coupled with the balloon. In some embodiments, the distal tip and/or the light guide may include a radiopaque marker A catheter having a first proximal end and a first distal end is provided according to another embodiment. The catheter may include a light guide lumen having a second distal end and a second proximal end, the second proximal end being substantially contiguous with the first proximal end, the second distal end having an opening. A distal tip may also be included having a third proximal end and a third distal end, the third proximal end being substantially contiguous with the second distal end. The catheter may include a balloon lumen having a fourth distal end and fourth proximal end, the fourth proximal end being substantially contiguous with the second distal end. A balloon may be coupled with the balloon lumen at the fourth distal end. A guidewire lumen may be included that extends through the distal tip.

In accordance with some embodiments, without limitation, the invention comprises a catheter having a catheter body including a central axis between a first proximal end and a first distal end. The housing has a lumen disposed between the first proximal end and the first distal end in communication with a cavity disposed proximate the first distal end. A laser delivery member is movable and at least partially disposed within the lumen having a second proximal end and a second distal end. A ramp is disposed at an angle to the central axis and proximate the first distal end of the catheter body within the cavity. The ramp is in communication with the lumen and is adapted to move the second distal end of the laser delivery member outwardly from the central axis of the elongated member. A guidewire is in mechanical communication with both the laser delivery member and the catheter body. The guidewire is adapted to bias the second distal end of the laser delivery member generally inwardly toward the central axis of the housing. In some embodiments, without limitation, the ramp is used to determine the offset of the central axis of the tip of the laser delivery member from the central axis of the housing, while keeping the axes substantially parallel, by adjusting the extent to which the laser delivery member travels on the ramp, and the disposition of the laser delivery member on the guidewire maintains the offset tip substantially parallel to the central axis of the housing. Methods of using same are also disclosed.

BRIEF DESCRIPTION OF THE DRAWINGS

The features and inventive aspects of the present invention will become more apparent upon reading the following detailed description, claims, and drawings, of which the following is a brief description:

FIG. 18A shows a side view of the distal end of a deflated balloon biasing catheter according to one embodiment.

FIG. 18B shows a side view of the distal end of a inflated balloon biasing catheter according to one embodiment.

FIG. 18C shows a side view of the distal end of a deflated balloon biasing catheter with a proximal guidewire port within the catheter body according to one embodiment.

FIG. 18D shows a side view of the distal end of a deflated balloon biasing catheter with a proximal guidewire port proximal with the distal tip according to one embodiment.

FIGS. 22A, 22B, and 22C show a cutaway view of a balloon biasing catheter in use within a vessel according to one embodiment.

DETAILED DESCRIPTION OF THE INVENTION

Figure 1:
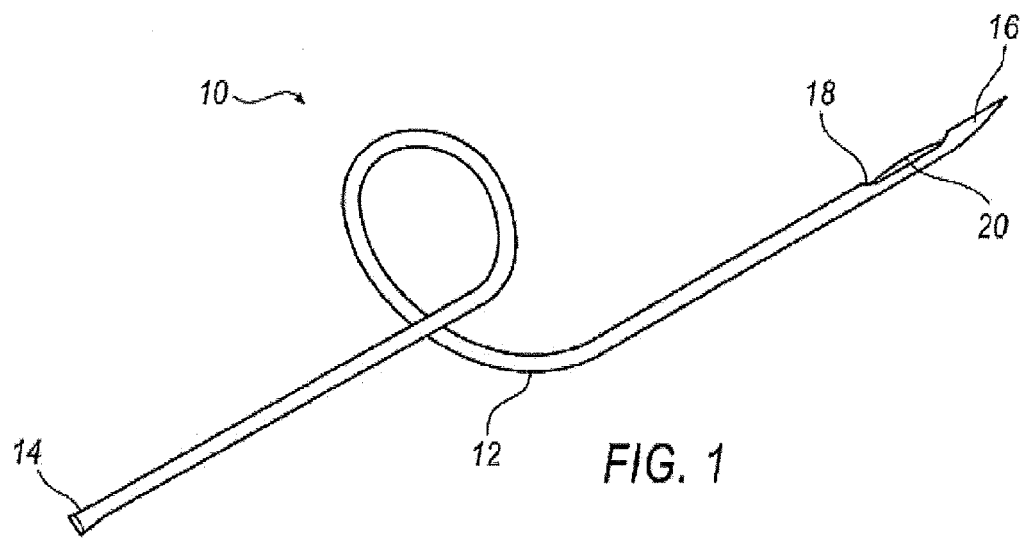
FIG. 1 is perspective elevated view of a catheter according to one embodiment.
Figures 2, 3:
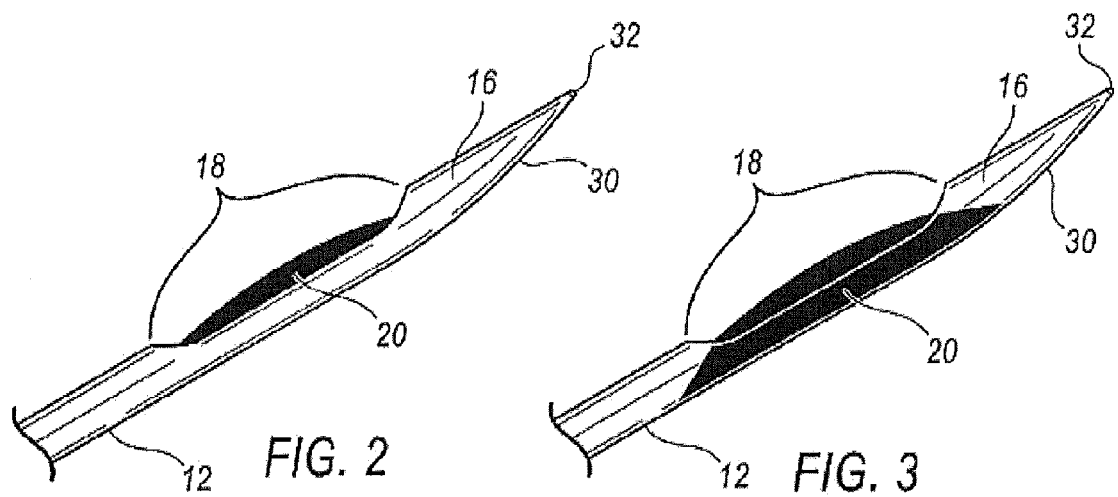
FIG. 2 is an exploded perspective view of a cavity of FIG. 1.
FIG. 3 is an exploded perspective view of FIG. 1 showing one embodiment of a ramp.
Figure 4:
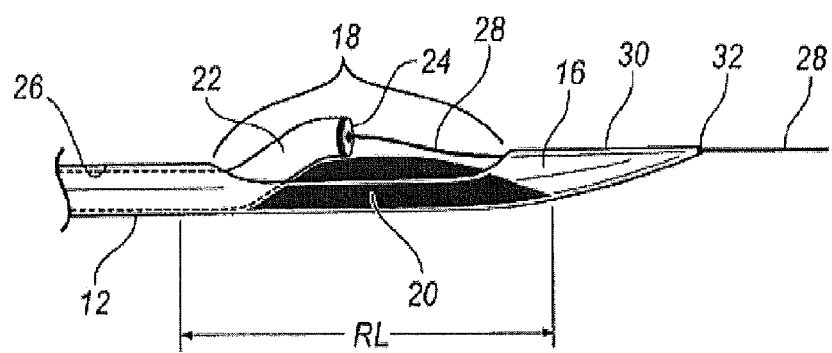
FIG. 4 is an exploded perspective view of FIG. 1 showing a ramp, a laser delivery member, and a guidewire.

Referring now to the drawings, illustrative embodiments are shown in detail. Although the drawings represent some embodiments, the drawings are not necessarily to scale and certain features may be exaggerated to better illustrate and explain an innovative aspect of an embodiment. Further, the embodiments described herein are not intended to be exhaustive or otherwise limit or restrict the embodiments of the invention to the precise form and configuration shown in the drawings and disclosed in the following detailed description.

Referring now to FIGS. 1-4, a catheter 10 is shown having an elongated housing 12. The elongated housing 12 includes a central axis between a first proximal end 14 and a first distal end 16. A cavity 18 is located proximate to the first distal end 16 of elongated housing 12 having a ramp 20 at an angle to the central axis of the housing 12. The angle of the ramp 20 may but need not be the same over the length of the ramp. In some preferred embodiments, without limiting the scope of the invention, the housing includes a tapering end 30 and a guidewire aperture 32 capable of accepting the guidewire 28. A laser delivery member 22 comprising one or more optical fibers capable of transmitting light energy is disposed within a lumen 26 of the housing 12 having a second proximal end (not shown) and a second distal end 24 movable therein. In some embodiments, without limitation, the laser delivery member 22 may be in mechanical communication with a guidewire 28 as further discussed below.

The guidewire 28 is threaded through a needle (not shown) into the artery and the needle is removed. The guidewire is advanced to or near the treatment site and may be inserted at its distal end into or across the lesion to be treated, as desired. The guidewire 28 serves as a tracking guide for the housing 12 and laser delivery member 22 to run on. Guidewires for such uses are known in the art and may comprise those with diameters between about 0.010 and 0.06 inches, with 0.014 and 0.018 inches diameter being typical sizes for artery applications. The guidewires may have bendable tips of coiled wire or plastic and a more rigid shaft of tapered ground stainless steel or other suitable material for push and torque transmission. The housing 12 and laser delivery member 22 are introduced coaxially, either sequentially or simultaneously, onto the guidewire 28 and advanced to a target area as further discussed below.

In some embodiments, without limitation, the housing 12 is introduced onto the guidewire 28 that has been inserted into the patient, and the housing is advanced to or near the treatment site such that portions of the guidewire 28 are disposed at least initially within the guidewire aperture 32, tapering end 30, and lumen 26 of the housing. The laser delivery member 22 is then introduced onto the guidewire 28 so disposed within the catheter 10. The laser delivery member 22 is then advanced along the guidewire 28 such that the distal end 24 of the laser delivery member 22 becomes supported by the ramp 20 and oriented within the cavity 18 at any angle between 1 degree and 90 degrees in relation to the central axis of the housing 12, as desired by the user. Laser energy is then applied to the treatment site according to methods and protocols known to those of ordinary skill in the art. In some embodiments, without limiting the scope of the invention, in conjunction with the application of laser energy, the position of the laser delivery member 22 may optionally be varied by the user by moving the member 22 proximally or distally in order to adjust the angle of disposition of its distal end 24. Optionally, the offset of the central axis of the tip of the laser delivery member 22 from the central axis of the housing 12 may be varied by adjusting the distance that the delivery member 22 travels on the ramp 20 while keeping the central axis of the tip substantially parallel to the central axis of the housing 12. In addition, the catheter 10 containing the laser delivery member 22 may optionally be rotated along its central axis during the laser treatment and thereby apply laser energy to areas of the treatment site within the are of the rotation. Optionally, the guidewire 28 may be withdrawn before application of laser energy and after the laser delivery member 22 has been introduced via the guidewire 28 into the lumen 26 of the housing 12.

The elongated housing 12 is an elongated structure having a lumen or lumen 26 large enough to accommodate the laser delivery member 22 and guidewire 28. The lumen 26 extends the entire length of the housing 12 from the first proximal end 14 to the first distal end 16. Optionally, in some embodiments, the lumen 26 may extend only to the ramp 20. Various control mechanisms including electrical, optical, and mechanical control mechanisms may be employed with the housing 12 permitting the catheter to be specifically directed to a target area (not shown) within the blood vessel. One embodiment of the housing includes a tapering end 30 and a guidewire aperture 32 capable of accepting the guidewire 28. The housing 12 may be made from any rigid, semi-flexible, or flexible material including a combination thereof made from a material including metal, plastic, rubber, and the like. Round or flat metal ribbon wire may be embedded within the material, inserted through the cavity 18, or disposed at the first distal end 16 to add stability to the housing 12 at the first distal end 16. The length of the housing 12 may be varied as desired. The housing 12 may be one piece or have a plurality of sections including a support structure section at the first distal end 16 as discussed further below. The distal end 16 of the housing 12 may include a non-traumatic polymer tip separate or integrated into the housing 12. This allows the forces seen in bending to be dissipated throughout the structure, reducing stress risers that could cause failure. The housing 12 may also include at least one wire disposed within the lumen 26 to add robustness to the housing 12. The lumen 26 is in communication with cavity 18 and wire aperture 32. The lumen 26 is open to the exterior of the housing 12 through the cavity 18.

The ramp 20 is disposed within cavity 18 and is configured to project the laser delivery member 22 outwardly at various determinable angles. Optionally, the ramp 20 is used to determine the offset of the central axis of the tip of the laser delivery member 22 from the central axis of the housing 20, while keeping the axes substantially parallel, by adjusting the extent to which the laser delivery member 22 travels on the ramp 20. In some embodiments without limitation, the disposition of the laser delivery member 22 on the guidewire 28 maintains the offset tip substantially parallel to the central axis of the housing 12. In some embodiments, without limitation, the angle of lateral deviation of the ramp 20 from central axis of the housing 12 will vary in range as desired from one (1) degree to ninety (90) degrees, more usually in the range from thirty (30) degrees to sixty-five (65) degrees. By employing ramp 20 having different exit angles from the associated lumen 26, different angles and/or offsets may be selected for treating a target area after the catheter 10 has been located within a patient. In some embodiments, without limitation, the ramp 20 may be adjustable, as one example only, by inflation of a balloon, and/or the ramp 20 may be slidable to allow varying degrees of offset.

The ramp 20 may be a built-up feature within the lumen 26 of the housing 12 and may be located anywhere along the longitudinal length of the housing 12, but preferably at or within about 3 cm from the first distal end 16 of the housing 12. The ramp 20 may be formed or fused to the internal wall of the housing 12 and made from metal, plastic, rubber, and the like. In one embodiment, the ramp length (RL) is generally 1 cm. However, the ramp length (RL) may also be varied.

The first distal end 16 of the housing 12 may be formed from plastic, metal, or any combination thereof. When metal is used, materials must be selected to provide appropriate flexibility without producing failure since the cavity 18 tends to reduce the structural integrity of some portions of the housing 12. Thus, in some embodiments, the first distal end 16 comprises a shape memory alloy, as one example only, nickel-titanium alloy. In other embodiments, without limitation, the first distal end 16 may comprise a stent-like structure proximal, distal, within, or a combination of such proximate the cavity 18. The stent-like structure may be made from at least one of stainless steel, cobalt-chromium, nickel titanium, and the like.

Figure 5:
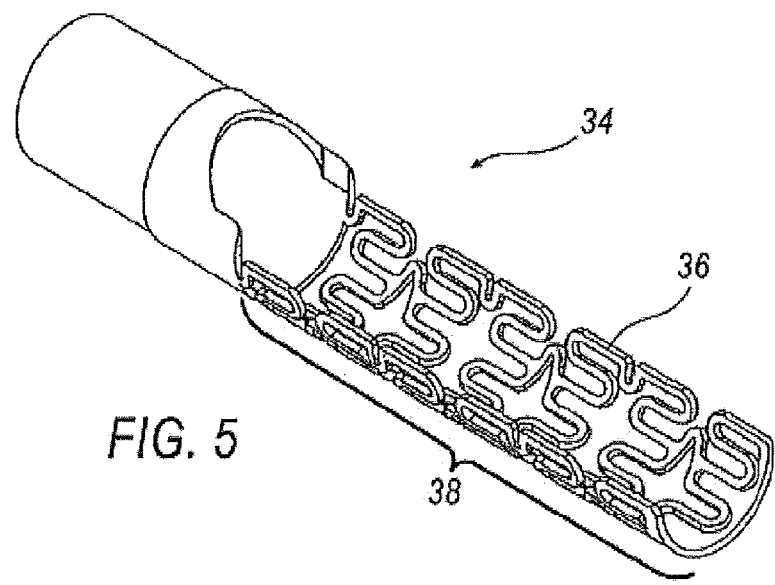
FIG. 5 is a perspective elevated view of a first embodiment of a support structure.
Figure 6:
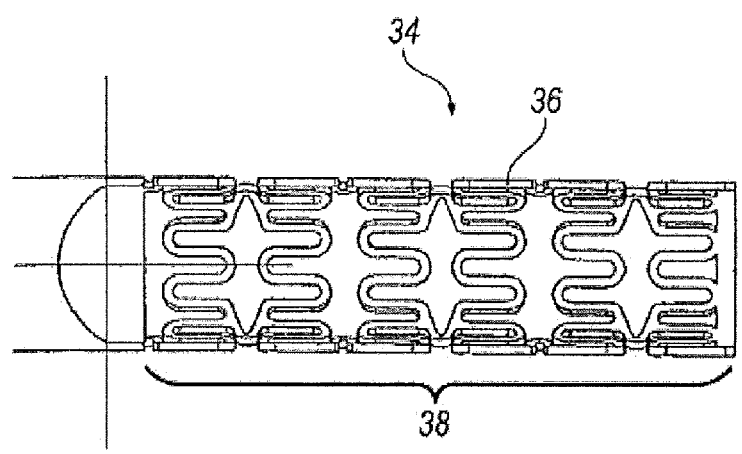
FIG. 6 is a top plan view of FIG. 5.
Figure 7:
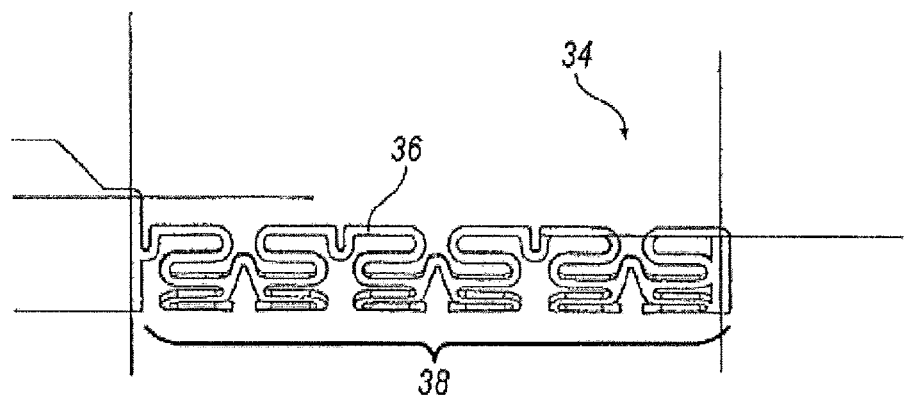
FIG. 7 is a side plan view of FIG. 5.

An alternative embodiment of the housing 12 comprises having at least one section at the first distal end 16. A first embodiment of a support structure is support member 34 as shown in FIGS. 5-7. The support member 34 may be used to support the first distal end 16 while providing flexibility without producing failure. The first distal end 16 of the housing 12 may otherwise experience limited torsional and bending strength of the area around the cavity 18 specifically traversing bends having a radius of about 0.75 inches. The support member 34 assists in withstanding the torsional and bending forces when traversing bends of about 0.75 inches, while maintaining aspects of both integrity and functionality. In some embodiments, without limitation, support member 34 reinforces the area around the cavity 18 at the first distal end 16 with struts 36 forming a stent-like pattern 38. Support member 34 is formed from metal, plastic, or combinations thereof, and is at least partially axially disposed around the wall of the first distal end 16 of the housing 12. The housing 12 may be one longitudinal piece or have a plurality of sections including the support structure as described above disposed at the first distal end 16 of the housing 12. Other embodiments of the support structure include a marker band proximate the first distal end 16 of the housing 12 and radiopaque markers at various intervals along the ramp 20 to demarcate acceptable ramp 20 positions for the catheter 10. As one example only, a user may place a catheter at a first mark on the ramp to increase the offset for ablation to 1 mm. A second mark might equal a 1.5 mm offset. This way the support structure may be used progressively, as one example only, as a progressive atherectomy tool. Additional embodiments having generally similar benefits may also be used, as further discussed below.

Figure 8:
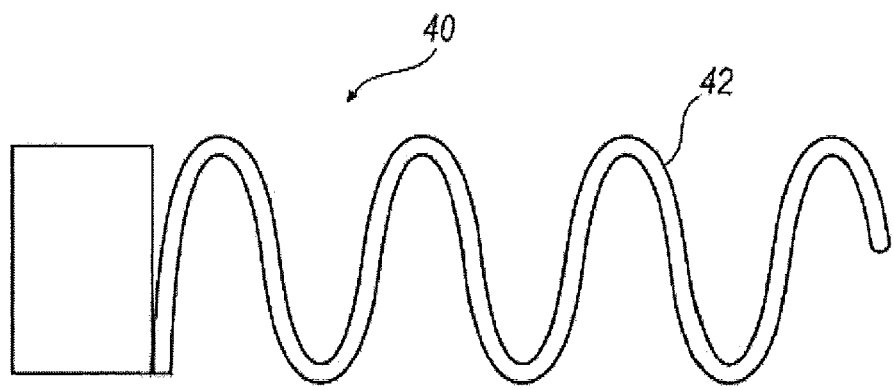
FIG. 8 is a top plan view of a second embodiment of a support structure.
Figure 9:
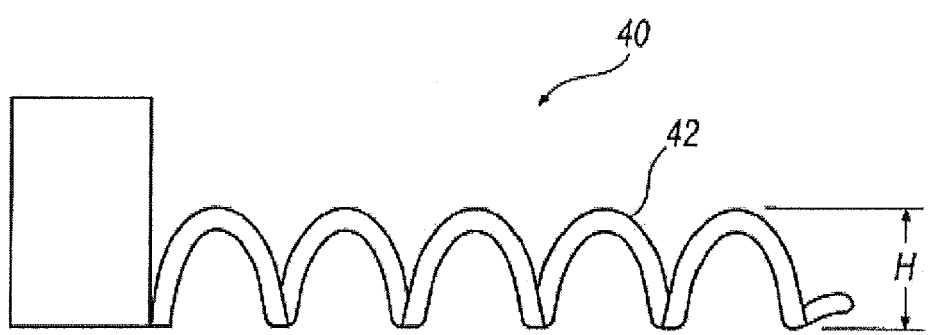
FIG. 9 is a side plan view of FIG. 8.

Referring to FIGS. 8 and 9, a second embodiment of a support structure is shown as second support member 40 having a spring-like geometry 42. The support member 40 may be used to support the first distal end 16 while providing flexibility without producing failure. The second support member 40 acts as a backbone for the first distal end 16 of the housing 12. The spring-like geometry 42 permits flexing without causing failure. The height H of the spring-like geometry 42 may be of any height but is preferably below the centerline of the second support member 40. The ramp 20 may be molded over the spring like geometry 42 including having a top coat (not shown).

Figure 10:
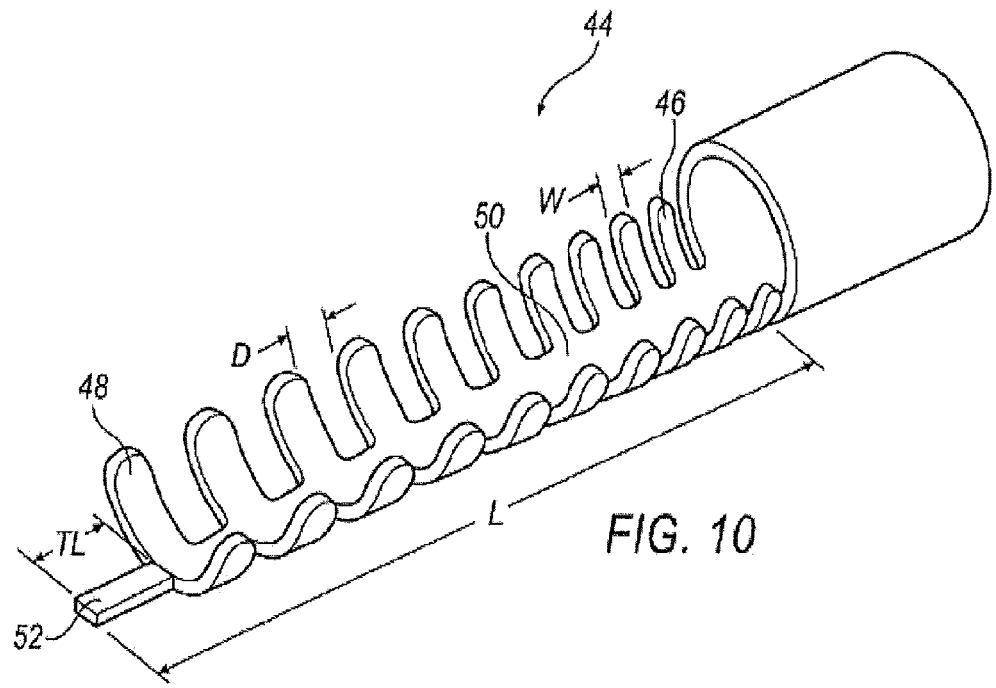
FIG. 10 is a perspective elevated view of a third embodiment of a support structure.
Figure 11:
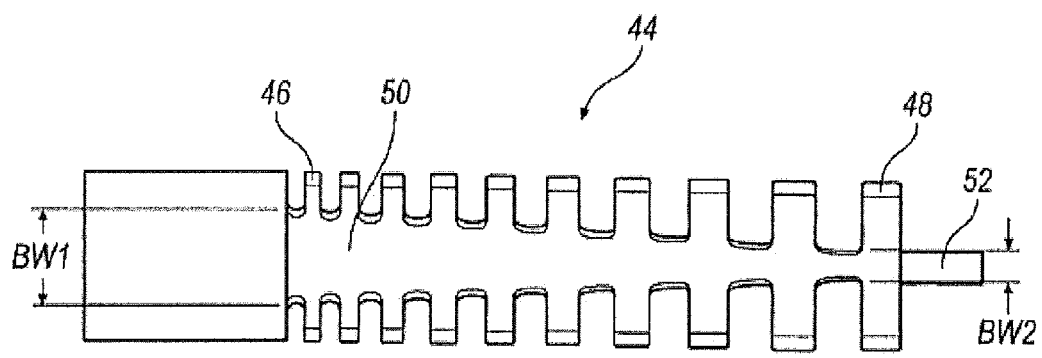
FIG. 11 is a top plan view of FIG. 10.

Referring to FIGS. 10 and 11, a third embodiment of a support structure is shown as a third support member 44. The support member 44 may be used to support the first distal end 16 while providing flexibility without producing failure. The third support member 44 provides variable stiffness along the length of the member 44. Member 44 is the most rigid at rib 46 and most flexible at rib 48. This flexibility is accomplished by having the ribs increase in width W and distance D in addition to decreasing the side of a beam 50 as shown in FIG. 11. Beam 50 tapers from a first wide beam width BW1 to a narrower beam width BW2. A tip 52 having a tip length TL disposed at the distal end support member 44 functions to provide support for the first distal end 16 of the housing 12 while allowing additional flexibility. The ramp 20 may be molded over the spring-like geometry 42 including having a top coat (not shown). The support member length L may be varied depending on user requirements including varying the tip length TL.

Figure 12:
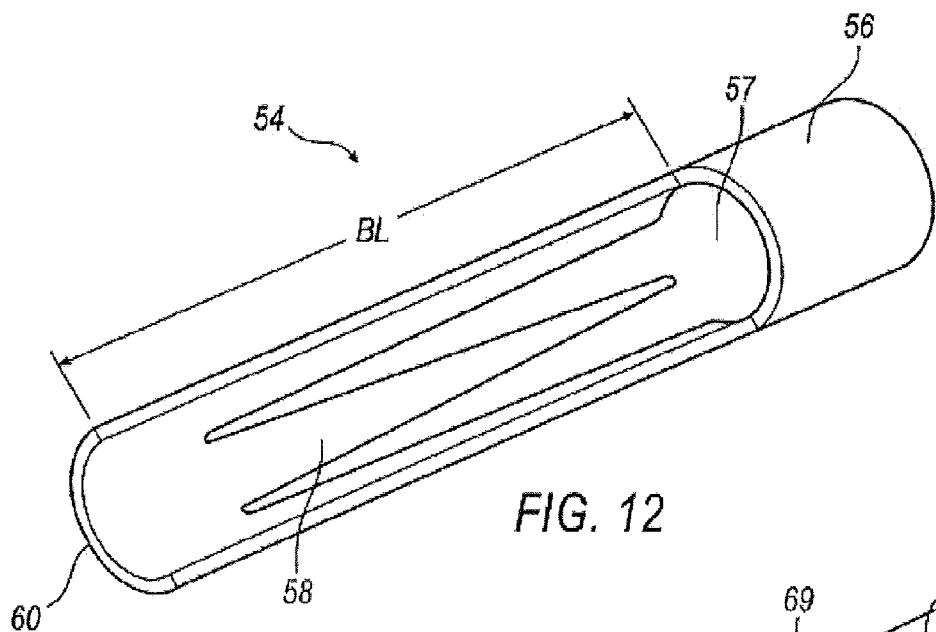
FIG. 12 is a perspective elevated view of a fourth embodiment of a support structure.

FIG. 12 shows a fourth embodiment of a support structure as fourth support member 54 disposed at the first distal end 16 of the housing 12. The support member 54 may be used to support the first distal end 16 while providing flexibility without producing failure. Support member 54 includes a rigid body 56 and a variably rigid base 58 extending from the body 56. Body 56 includes an aperture 57 in communication with lumen 26. The base 58 may be elastomeric having the greatest flexibility at distal end 60. The ramp 20 may be molded over the base 58 including having a top coat (not shown). The support member base length BL may be varied according to user requirements.

Figure 13:
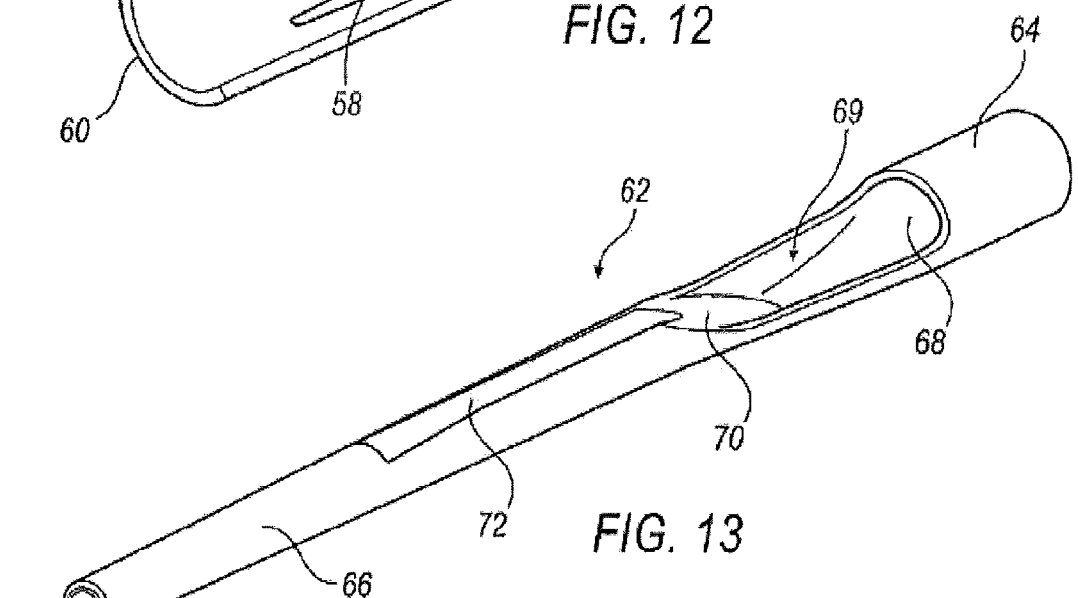
FIG. 13 is a perspective elevated view of a fifth embodiment of a support structure.

FIG. 13 shows a fifth embodiment of a support structure as fifth support member 62. The support member 62 includes a rigid body 64 having a flexible tapered nose portion 66. At least the nose portion 66 may be comprised of elastomeric material, as one example only, Rebax 55D available from Arkema. The body 64 is configured to communicate with the first distal end 16 of the housing 12. An aperture 68 is disposed within body 64 in communication with lumen 26 of the housing 12 and is configured to accommodate both the laser delivery member 22 and guidewire 28. Aperture 68 is also in communication with the nose widow 69. The nose window 69 of the nose portion 66 includes a nose ramp 70 configured to project the laser delivery member 22 outwardly at various predetermined angles. Optionally, the ramp 20 is used to determine the offset of the central axis of the tip of the laser delivery member 22 from the central axis of the housing 20, while keeping the axes substantially parallel, by adjusting the extent to which the laser delivery member 22 travels on the ramp 20. In some embodiments without limitation, the disposition of the laser delivery member 22 on the guidewire 28 maintains the offset tip substantially parallel to the central axis of the housing 12. Usually, the angle of lateral deviation of the ramp 20 from the housing 12 will vary in range as desired from one (1) degree to ninety (90) degrees, more usually in the range from thirty (30) degrees to sixty-five (65) degrees. The nose portion also includes a nose lumen 72 and a nose guidewire aperture 74. The guidewire 28 disposed within and in mechanical communication the laser delivery member 22 extends outwardly from the second distal end 24 of the laser delivery member 22 and is guided through the nose lumen 72 and extending out the guidewire aperture 74. Both the nose lumen 72 and guidewire aperture 74 provide securement for the guidewire 28 so that the guidewire 28 may properly bias the second distal end 24 of the laser delivery member 22 generally inwardly toward the central axis of the body 64.

Figure 14:
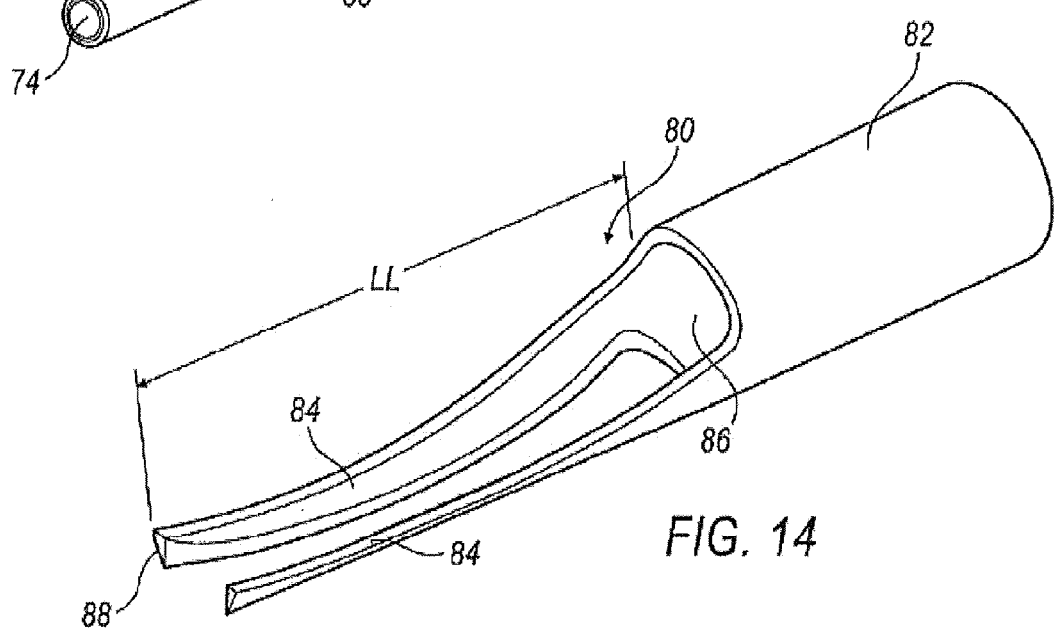
FIG. 14 is a perspective elevated view of a sixth embodiment of a support structure.

FIG. 14 shows a sixth embodiment of a support structure as sixth support member 80. The support member 80 may be used to support the first distal end 16 while providing flexibility without producing failure. Support member 80 includes a rigid body 82 and at least two variably rigid legs 84 extending from the body 82. Body 82 includes an aperture 86 in communication with the lumen 26. The body 82 may be elastomeric having the greatest flexibility at distal end 88. The legs 84 may be of any shape extending from the body 82. The ramp 20 may be molded over the legs 84 including having a top coat (not shown). The support member leg length LL may be varied depending on user requirements.

Figure 15:
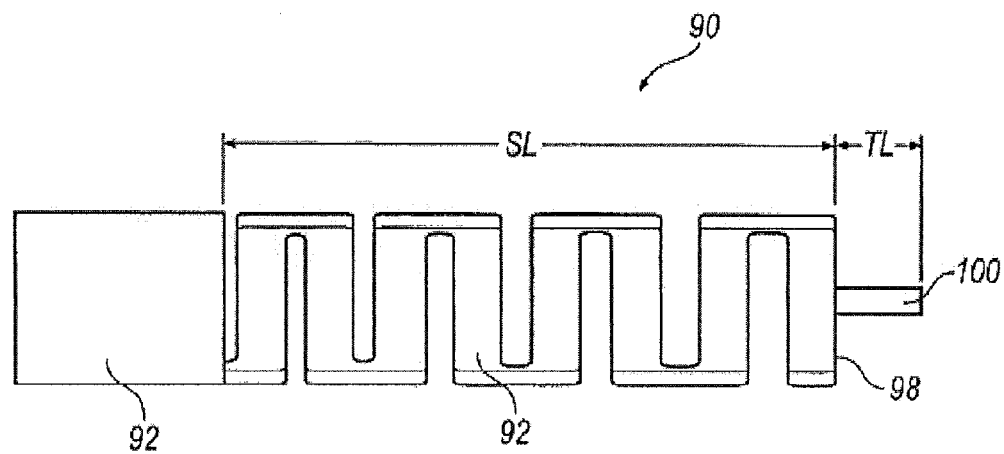
FIG. 15 is a top plan view of a seventh embodiment of a support structure.
Figure 16:
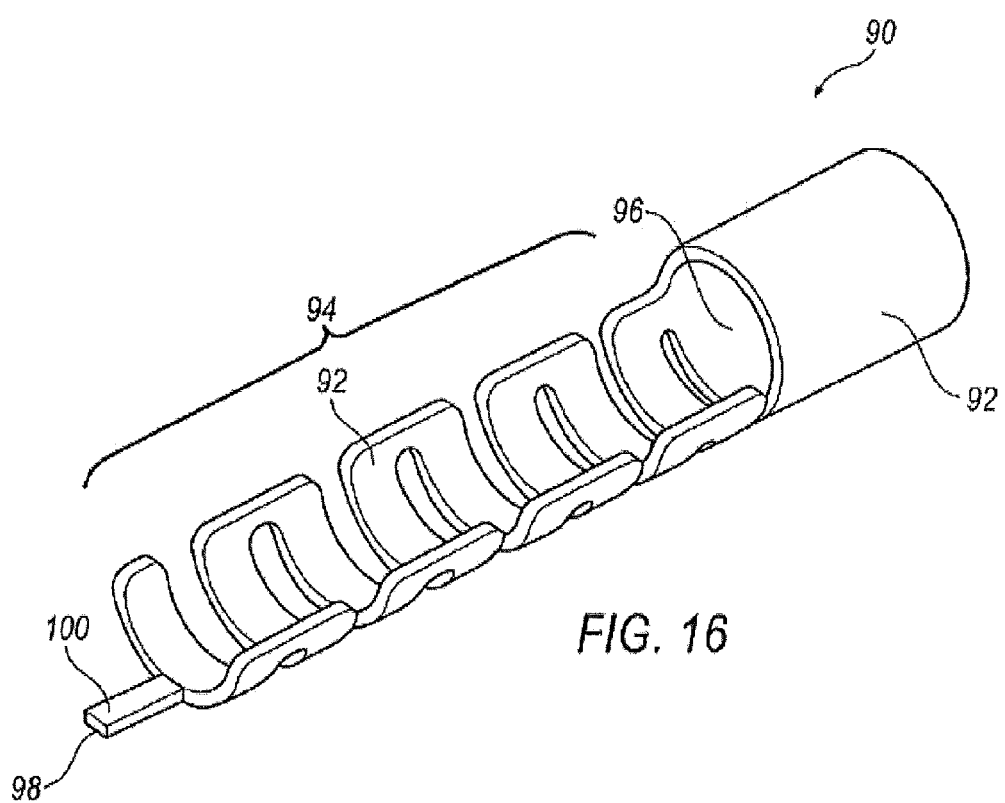
FIG. 16 is a perspective elevated view of FIG. 15.

FIGS. 15 and 16 show a seventh embodiment of a support structure as seventh support member 90. The support member 90 may be used to support the first distal end 16 while providing flexibility without producing failure. The first distal end 16 of the housing 12 may otherwise experience limited torsional and bending strength of the area around the cavity 18 specifically traversing bends having a radius of about 0.75 inches. The support member 90 assists in withstanding the torsional and bending forces when traversing bends of about 0.75 inches while maintaining both integrity and functionality. Support member 90 reinforces the area around the cavity 18 at the first distal end 16 with a braid 92 forming a stent-like pattern 94. Support member 90 is formed from metal or plastic and is at least partially axially disposed around the wall of the first distal end 16 of the housing 12. The housing 12 may be one longitudinal piece or have a plurality of sections including the support structure as described above disposed at the first distal end 16 of the housing 12. Support member 90 includes a rigid body 92 and a variably rigid base 94 forming the stent-like pattern 94 extending from the body 92. Body 92 includes an aperture 96 in communication with lumen 26. The base 94 may be elastomeric having the greatest flexibility at distal end 98. A tip 100 having a tip length TL disposed at the distal end support member 90 functions to provide support for the first distal end 16 of the housing 12 while allowing additional flexibility. The ramp 20 may be molded over the base 94 including having a top coat (not shown). The support member stent-like length SL may be varied depending on user requirements.

In operation, once the guidewire 28 is in place, or as it is being positioned, the housing 12 is inserted. This housing 12 has a central lumen 26, which may include the laser delivery member 22 and guidewire 28. The housing 12 and the laser delivery member 22 are advanced through the guidewire into the desired target area. Therefore, the guidewire 28 is in mechanical communication with both the laser delivery member 22 and the elongated housing 12. However, the housing 12 may be advanced prior to inserting the laser delivery member 22. As the laser delivery member 22 approaches the ramp 20, it is biased in an outwardly direction through the cavity 18. The further the laser delivery member 22 is advanced, the more it projects outwardly from the cavity 18 at the first distal end 16 of the housing 12. In some embodiments, without limitation, the guidewire 28 disposed within the laser delivery member 22 biases the second distal end 24 of the laser delivery member 22 inwardly providing a travel path and forcing the second distal end 24 to face forward along the guidewire 28 and generally parallel to the centerline of the housing 12. Otherwise, the second distal end 24 of the laser delivery member 22 would continue along the ramp 20 further projecting away from the centerline of the housing 12 and would not be "attacking" the target area in front of the catheter 10 as desired.

Figure 17:
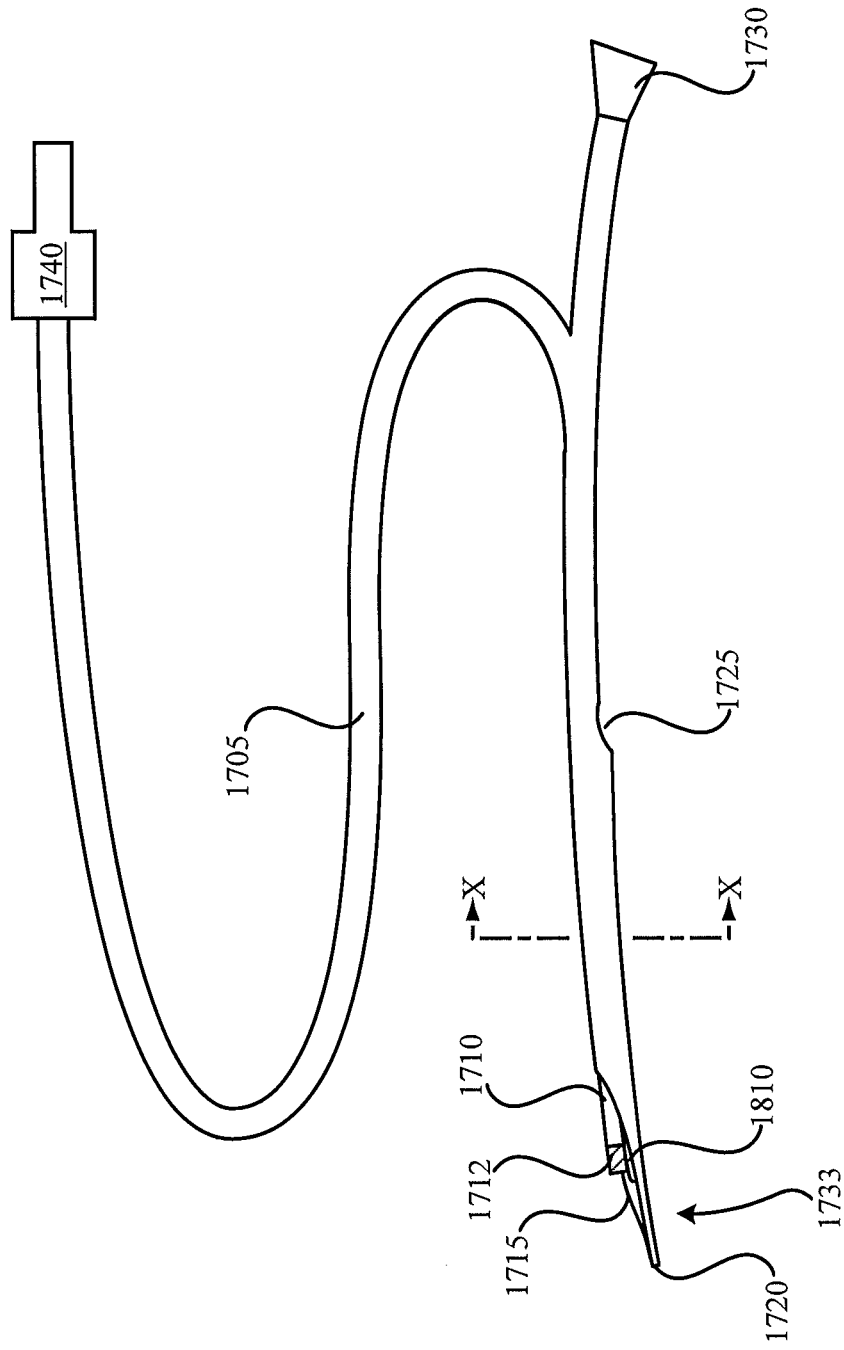
FIG. 17 is a side view of a balloon biasing catheter according to one embodiment.

FIG. 17 is a side view of a balloon biasing catheter according to one embodiment. A balloon biasing catheter may include a catheter body 1705 (or elongated housing) with a light guide 1710 disposed within a lumen of catheter body 1705 and extending from an aperture within catheter body 1705. For example, light guide 1710 may include a plurality of fiber optics. As another example, the light guide may be a liquid light guide and/or a combination of a liquid light guide and a fiber optic light guide. In some embodiments, the light guide is free to slide within the lumen of the catheter body. In some embodiments, the light guide lumen may slide relative to the catheter body. In other embodiments, the light guide may be fixed within the lumen of the catheter body. Light guide 1710 may be located within catheter body 1705 and may extend from the proximal end of the catheter body to the distal end of the catheter body. At the proximal end of the catheter body, light guide 1710 may be coupled with a laser coupler. The light guide lumen may include an aperture at or near the distal end of catheter body 1705 from which light guide 1710 may extend. In some embodiments, light guide 1710 may extend 1-10 mm from the aperture. In some embodiments, light guide 1710 may also include a radiopaque marker band 1712 near the distal end.

A balloon biasing catheter may also include a guidewire lumen. The guidewire lumen may be configured to allow a guidewire to pass and/or slide therethrough. In some embodiments, the guidewire lumen may extend, for example, from distal guidewire port 1720 through a portion of catheter body 1705. In some embodiments, the guidewire lumen may extend to or near the proximal end of catheter body 1705. In other embodiments, guidewire lumen may extend from the distal end to a position proximal with the light guide aperture and/or proximal with balloon 1810. The guidewire lumen may be configured to accept a guidewire and allow the guidewire to slide within the guidewire lumen 1812. Proximal guidewire port 1720 may be located any where along catheter body 1705.

FIG. 18A shows a side view of the distal end of a balloon biasing catheter with a deflated (or partially deflated) balloon. Distal tip 1733 extends beyond the catheter body. In some embodiments, distal tip 1733 may be integral with catheter body 1705; for example, distal tip 1733 may be manufactured as part of catheter body 1705. In some embodiments, distal tip 1733 extends beyond the aperture of the light guide lumen. In some embodiments, distal tip 1733 may be contiguous and/or coterminal with a peripheral portion of the catheter body. Guidewire lumen 1812 extends through distal tip 1733 and terminates at distal guidewire port 1720. Accordingly, in some embodiments, a balloon biasing catheter may slide over a previously placed guidewire by introducing the proximal end of the guidewire through distal guidewire port 1720, into guidewire lumen 1812, and then sliding the balloon biasing catheter over the guidewire within guidewire lumen 1812. The proximal end of the guidewire may then exit the balloon biasing catheter through proximal guidewire port 1725. Distal tip 1733 may also include a radiopaque marker 1805.

Distal tip 1733 may also include balloon 1810. Balloon 1810 may be located between distal tip 1733 and the distal end of light guide 1710. In some embodiments, distal tip 1733 may include a shelf-like structure upon which balloon 1810 may be positioned. Balloon 1810 may be coupled with a balloon lumen (or tube) 1813. Balloon lumen 1813 may extend to balloon port 1730. Balloon 1810 may be inflated and/or deflated by pressurizing balloon lumen 1813 with liquid using balloon port 1730. By inflating balloon 1810, light guide 1710 may be biased away from the central axis of catheter body 1705 as shown in FIG. 18B. It should be noted, that in some embodiments light guide 1710 remains relatively parallel with the central axis of catheter body 1705 and/or distal tip 1733 when balloon 1810 is inflated. As will be discussed, retaining wire 1715 aids in keeping light guide 1710 relatively parallel with catheter body 1705. Balloon 1810, for example, may deflect light guide 1710 1.0 mm. In other embodiments, light guide 1710 may be biased 0.5 mm, 1.5 mm, 2.0 mm, 2.5 mm, 3.0 mm etc. away from the central axis of catheter body 1705. By biasing the light guide, the balloon biasing catheter may ablate a larger diameter area than if the light guide is not biased.

Balloon lumen may couple with a luer fitting at balloon port 1730. Balloon port 1730 may be proximate with catheter body 1705 as shown. In some embodiments, balloon lumen may bifurcate with the catheter body and may extend a distance away from the catheter body. Balloon lumen 1813 may include a small diameter lumen. For example, the inner diameter of balloon lumen may be approximately 0.001 inches. In some embodiments, the inner diameter of balloon lumen 1813 may be between 0.0005 and 0.01 inches. The outside diameter of balloon lumen 1813, for example, may be 0.016 inches. In some embodiments, the outside diameter of balloon lumen 1813 may be 0.05 to 0.005 inches. At balloon port 1730 or luer, balloon lumen 1813 may be coupled with a syringe or an indeflator. Balloon 1810 may be inflated by injecting fluid through balloon lumen 1813 using either a syringe or an indeflator. In some embodiments, the balloon may be inflated using a contrast agent fluid or saline solution. Balloon lumen 1813 may include any type of plastic tubing known in the art. For example, balloon lumen 1813 may comprise nylon, Teflon, polyethylene, etc.

Balloon 1810 may have a diameter of about 1 mm to 3 mm when inflated, according to one embodiment. In some embodiments, balloon may have an inflated diameter up to about 5 mm and as little as 0.5 mm. In some embodiments, balloon 1810 may comprise a portion of tubing with a sealed distal end. In some embodiments, a portion of tubing may form balloon 1810 and have thinner walls and/or a larger diameter such that the balloon portion of the tubing inflates under pressure. Balloon 1810, for example, may comprise any type of plastic, for example, balloon 1810 may comprise nylon, Teflon, polyethylene, etc. Balloon 1810, in some embodiments, may extend the entire length of distal tip 1733. For example, balloon 1810 may be 10 cm, 9 cm, 8 cm, 7 cm, 6 cm, 5 cm, 4 cm, 3 cm, 2 cm, or 1 cm in length.

Retaining wire 1715 may be detachably coupled with either or both distal tip 1733 and/or light guide 1710. For example, retaining wire 1715 may be connected with the distal tip using solder, clamps, glue, fused, etc. In some embodiments, retaining wire is soldered with radiopaque marker band 1712. In other embodiments, retaining wire 1715 may be coiled around the distal tip and glued or fused with distal tip 1733. In some embodiments, retaining wire 1715 may be sandwiched between distal tip 1733 and radiopaque marker band 1712. In some embodiments, retaining wire 1715 may extend through a portion of light guide 1710 as shown in FIG. 18A. For example, retaining wire 1715 may extend through light guide 1710 next to and/or with a plurality of optical fibers. Retaining wire 1715 may aid in retaining the position and/or bias of the light guide when balloon 1810 is deflated. Retaining wire 1715 may also aid in providing the proper bias when balloon 1810 is inflated. For example, retaining wire may lengthened and/or include elasticity such that balloon biasing catheter may be more or less biased when balloon 1810 is inflated. In some embodiments, retaining wire provides resistance to light guide 710 when balloon 1810 is inflated, which may align light guide 1710 parallel with distal tip 1733 and/or catheter body 1705.

FIG. 18C shows a side view of the distal end of a balloon biasing catheter with a deflated (or partially deflated) balloon with proximal guidewire port 1822 disposed more toward the proximal end of the balloon biasing catheter than the distal end of light guide 1710 and balloon 1810. FIG. 18D shows proximal guidewire port 1822 disposed proximate with distal end of light guide 1710 and balloon 1810.

Figure 19:
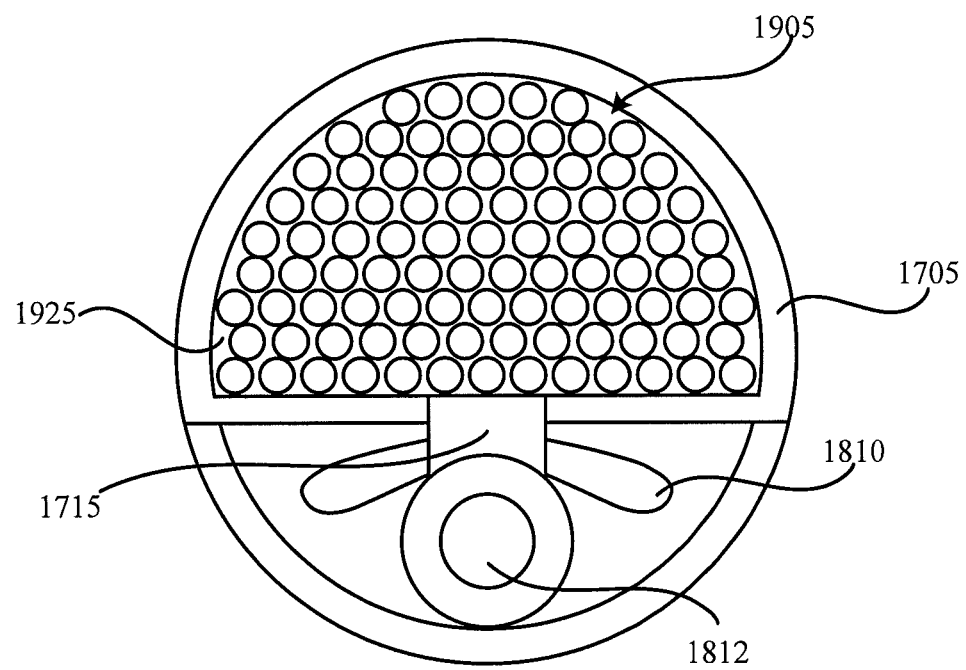
FIG. 19 shows an end view of the distal tip of a balloon biasing catheter according to one embodiment.

FIG. 19 is an end view of the balloon biasing catheter shown in FIG. 18A according to one embodiment. A catheter sheath 1705 (or elongated housing or catheter body) is shown containing a plurality of optical fibers 1905. In some embodiments, catheter sheath 1705 may have a diameter of approximately 2.0 mm. Each of the fibers, for example, may be less than about 0.1 mm. As another example, the fibers may be less than about 0.05 mm. The fiber optics may be contained within lumen 1911. For example, lumen 1911 may be about 1.0 mm by about 2.0 mm. Guidewire lumen 1910 is located beneath lumen 1911. Guidewire lumen 1910, for example, may have an inside diameter of approximately 0.024 inches and inside diameter 0.018 inches. In other embodiments, guidewire lumen 1812 may have an outside diameter less than about 0.025 inches and/or an inside diameter less than about 0.02 inches.

Figure 20:
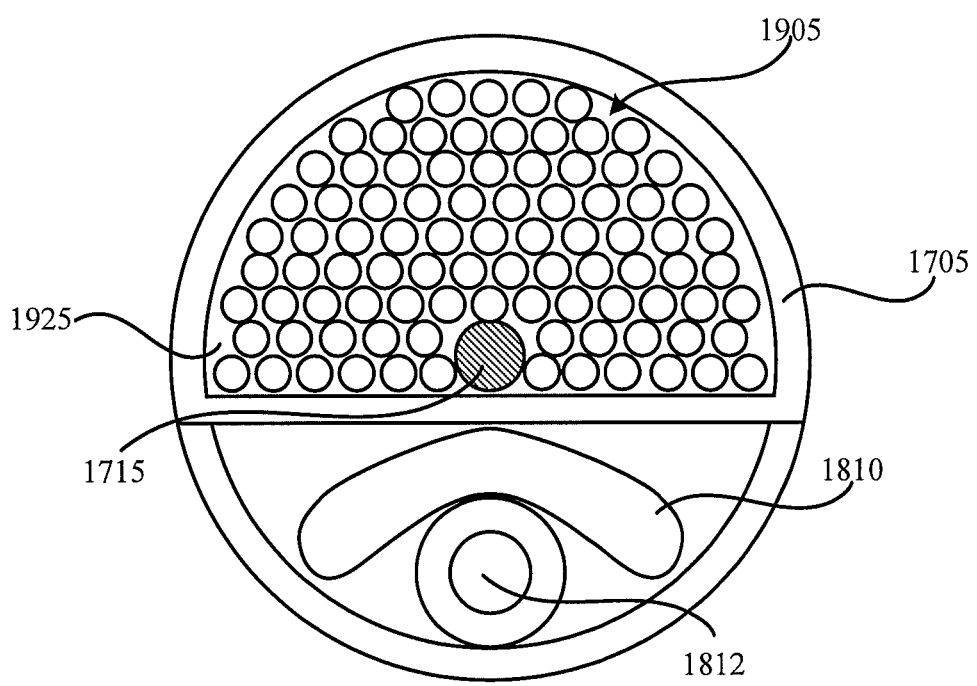
FIG. 20 is a cutaway view of the distal tip of a balloon biasing catheter according to one embodiment.

Balloon 1810 may be positioned between guidewire lumen 1812 and optical fiber lumen 1911. Retaining wire 1715 is also shown. In the embodiment shown in FIG. 19, retaining wire 1715 is a flat wire. In other embodiments, retaining wire 1715 may be any type of wire, such as a round, rectangular, square and/or oval shaped wire. In FIG. 20 optical fiber lumen 1925 may be a separate round and/or oval shaped lumen and may be found within a tube. Moreover, other retaining device may be employed that retain a first bias of the that is generally parallel with the central axis of the catheter sheath when the balloon is deflated and permit a radial bias of the catheter tip when the balloon is inflated.

FIG. 20 is a cutaway view of the distal tip of a balloon biasing catheter according to one embodiment. This cutaway view is provided along line Y-Y in FIG. 18A. As shown in this embodiment, retaining wire 1715 is disposed within optical fiber lumen 1925. In some embodiments, retaining wire 1715 extends, for example, about 1 cm into optical fiber lumen 1925. In some embodiments, retaining wire 1715 can run the distance of the catheter body toward the proximal end and be secured at a termination point.

Figure 21:
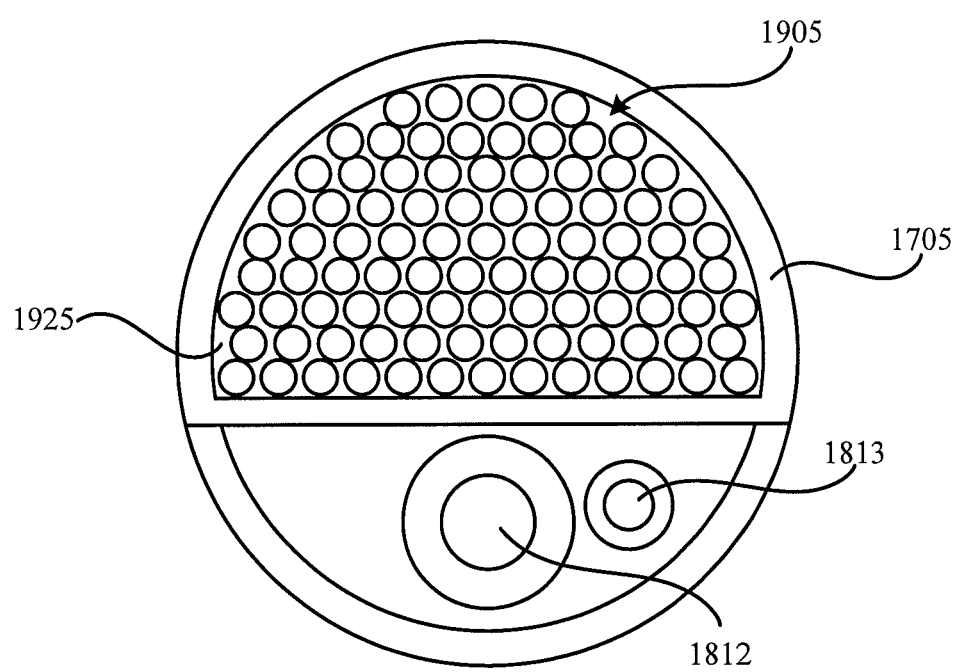
FIG. 21 is a cutaway view of balloon biasing catheter showing a light guide, balloon lumen and guidewire lumen according to one embodiment.

FIG. 21 is a cutaway view of balloon biasing catheter showing a optical fiber lumen 1925, balloon lumen 1813 and guidewire lumen 1812 within catheter sheath according to one embodiment. Balloon lumen 1813 may be disposed within a tube or other hollow member. Guidewire lumen 1812 may also be disposed within a tube or other hollow member. This cutaway view is provided along line Z-Z in FIG. 18A and/or X-X in FIG. 17.

FIG. 22A shows a cutaway of a balloon biasing catheter in use within vessel 2200 near target 2205. The balloon biasing catheter may be inserted into vessel 2200 by following guidewire 2220. Guidewire 2220 may run through the guidewire lumen as shown in the figure. Balloon 1810 is deflated in FIG. 22A. Light guide 1710 may be activated and a portion of target 2220 may be ablated. FIG. 22B shows target 2205 after ablation with balloon biasing catheter positioned as shown in FIG. 22. Target 2205 may not be completely ablated leaving target portions 2210 and 2215. In some embodiments, a hole within target 2210 may result.

Figure 22C:
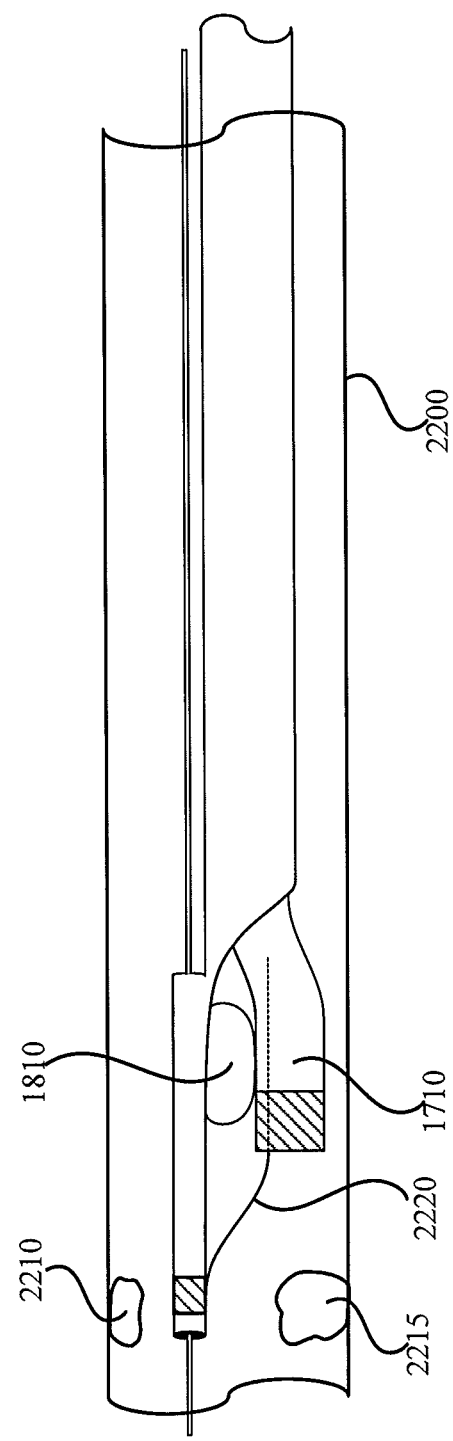

FIG. 22B shows light guide 1710 biased axially by inflating balloon 1810. When balloon 1810 is inflated, light guide 1710 may be in position to ablate at least some of target portion 2210. Moreover, balloon 1810 may be partially or fully inflated as needed to align light guide 1710 with target portion 2210. FIG. 22C shows a resulting example of ablation using the configuration in FIG. 22B. Target portion 2210 has been partially ablated. In some embodiments, target portion 2210 may be completely ablated. FIG. 22C also shows balloon biasing catheter rotated within vessel 2200 about 180° and positioned to ablate target portion 1715. In some embodiments, balloon 1810 may be deflated prior to rotation and reinflated after rotation. In some embodiments, balloon biasing catheter and/or guidewire 2220 may be advanced during any of the ablation steps. In some embodiments, balloon biasing catheter may be rotated 90° or any other angle in order to ablate other target portions and/or material near or adhering to a vessel wall.

Figure 23:
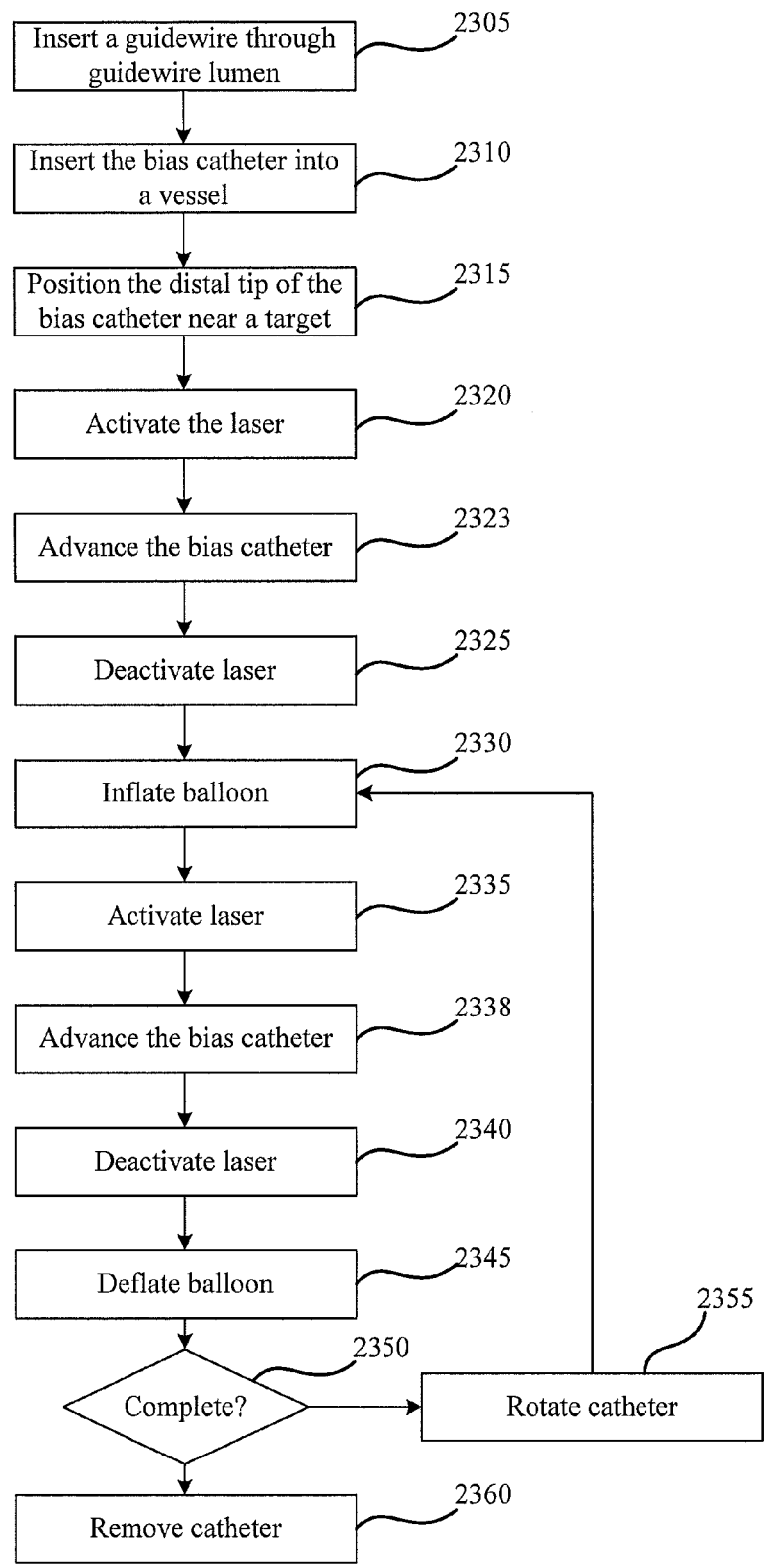
FIG. 23 is a flowchart describe one embodiment for using a balloon biasing catheter.
Figure 24:
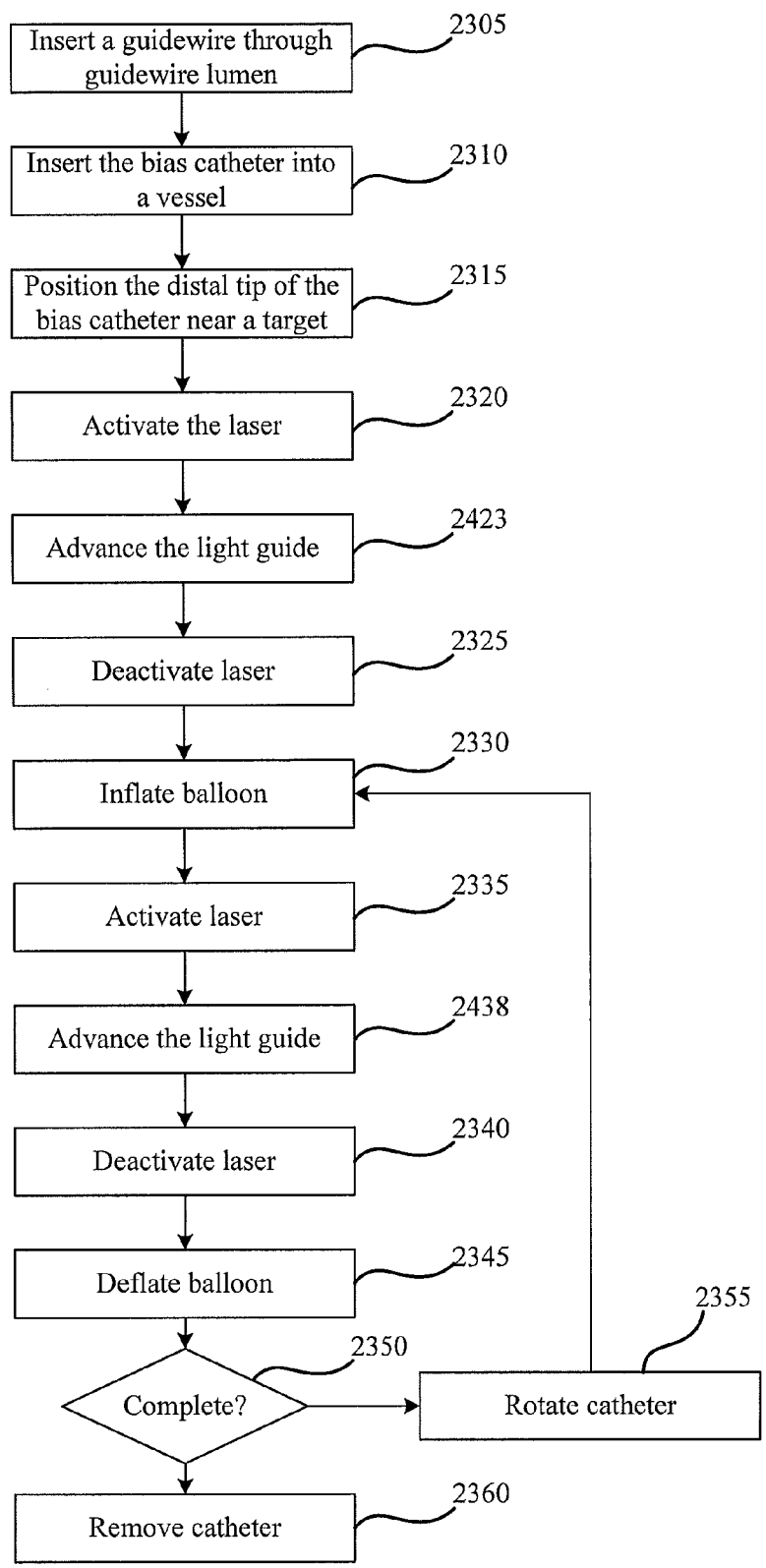
FIG. 24 is another flowchart describe one embodiment for using a balloon biasing catheter.

FIG. 23 shows a flowchart of a process for using a balloon biasing catheter according to one embodiment. Various other processes may be used that add to or take away from the process shown in FIG. 23 and described below. The proximal end of a guidewire is inserted through the distal guidewire port at the distal tip of the balloon biasing catheter at block 2305. The balloon biasing catheter may then be inserted into a vessel at block 2310 and slid over the guidewire and positioned near a target at block 2315. At block 2320 the laser may be activated ablating a portion of the target area. The balloon biasing catheter may be advanced at block 2323. Once ablation is complete, the laser is deactivated at block 2325. If portions of the target are not completely ablated, for example, if material remains near the vessel walls, then the balloon may be inflated at block 2330. When the balloon is inflated the distal tip of the balloon biasing catheter may be radially biased yet substantially parallel with the balloon biasing catheter and positioned to ablate unablated portions of the target. The laser may again be activated at block 2335 and portions of the target ablated. At block 2338 the balloon biasing catheter may be advanced toward the target. At block 2340 the laser is deactivated after a period of time and the balloon deflated at block 2345. If the ablation area is satisfactory and no more ablation is required as decided at block 2350 the balloon biasing catheter is removed at block 2360. However, if more ablation is required, the balloon biasing catheter may be rotated axially within the vessel at block 2355 and the process returns to block 2330.

FIG. 23 shows a flowchart of a process for using a balloon biasing catheter according to one embodiment. This flow chart is substantially similar to the flowchart shown in FIG. 23. In this embodiment, however, at blocks 2423 and 2438 the light guide is advanced relative to the balloon biasing catheter. In such embodiments, the catheter body remains substantially still as the light guide is advanced to ablate target material.

Figure 25:
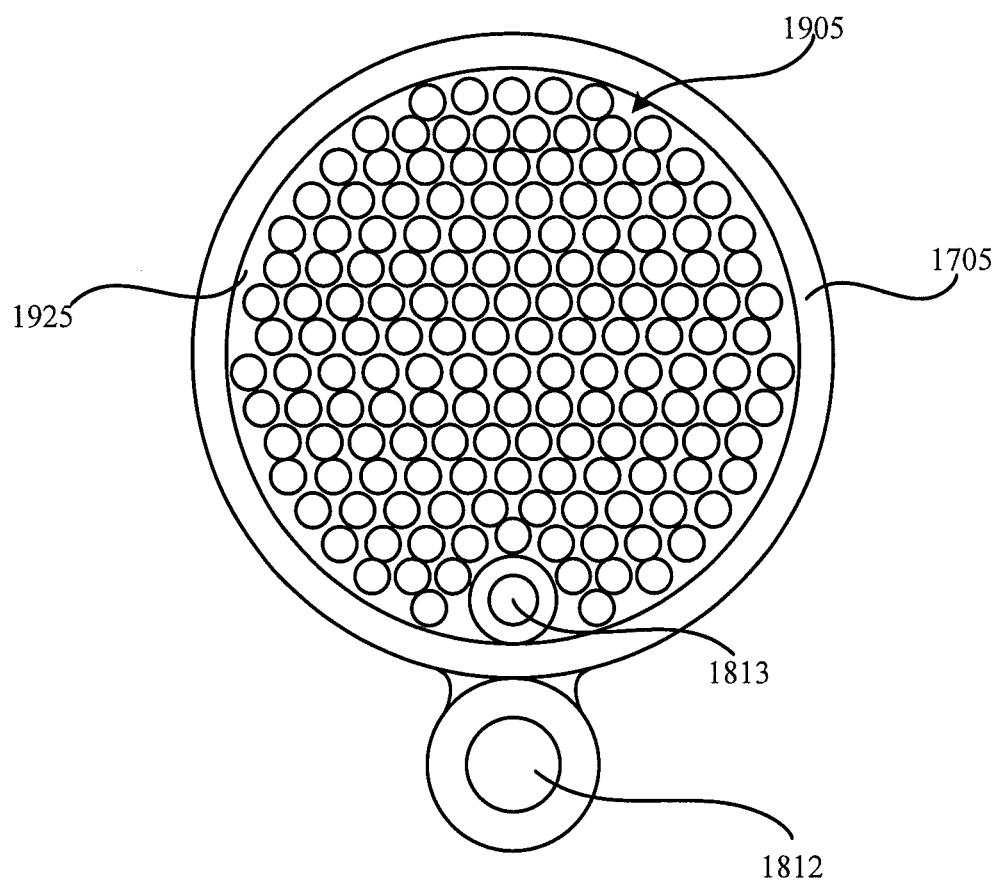
FIG. 25 shows a cutaway view of the distal tip of a balloon biasing catheter according to one embodiment.

FIG. 25 shows a cutaway view of a balloon biasing catheter according to one embodiment. For example, this cutaway view may be cut along lines X-X, or Z-Z in FIG. 18A. As shown, the guidewire lumen 1812 is shown exterior to and attached with catheter body 1705. The guidewire lumen 1812 may be disposed as shown within a tube. Moreover, guidewire lumen 1812 may be disposed anywhere within optical fiber lumen 1925. Balloon lumen 1813 in this embodiment is disposed within optical fiber lumen 1925 along with a plurality of optical fibers 1905. In other embodiments, balloon lumen may be disposed external to the catheter body 1705 either with or without the guidewire lumen 1812.

The preceding description has been presented only to illustrate and describe exemplary embodiments of the methods and systems of the present invention. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope.

What is claimed is:

1. A method comprising:
   positioning a catheter within a vessel, wherein the catheter comprises:
      a catheter body having a central axis, a proximal end and a distal end, the catheter body having a lumen disposed between the proximal end and the distal end, the lumen having an opening at the distal end;
      a light guide having a proximal end and a distal end, the light guide being at least partially disposed within the lumen and movable therein, wherein the light guide is coupled to a laser;
      a tip distally extending from the distal end of the catheter body;
      a retaining wire coupled with the tip and slidably positioned with the light guide; and
      a balloon positioned within the opening;
   inflating the balloon, wherein the balloon cooperates with the retaining wire to adjust the distal end of the light guide into a position substantially parallel with the tip of the catheter body; and
   activating the laser to ablate material within the vessel.

2. The method of claim 1, wherein activating the laser to ablate material includes advancing the catheter within the vessel while the laser is activated.

3. The method of claim 2, further comprising:
   deactivating the laser after advancing the catheter within the vessel; and
   deflating the balloon after deactivating the laser.

4. The method of claim 3, further comprising:
   rotating the catheter within the vessel after deflating the balloon;
   reinflating the balloon after rotating the catheter; and
   reactivating the laser to ablate material within the vessel after reinflating the balloon.

5. The method of claim 1, wherein activating the laser to ablate material includes activating the laser to ablate material after inflating the balloon.

6. The method of claim 5, wherein activating the laser to ablate material after inflating the balloon includes rotating the catheter within the vessel while the laser is activated.

7. The method of claim 5, wherein activating the laser to ablate material after inflating the balloon includes advancing the catheter within the vessel while the laser is activated.

8. The method of claim 7, further comprising:
   deactivating the laser after inflating the balloon, activating the laser, and advancing the catheter; and
   deflating the balloon after deactivating the laser;
   rotating the catheter within the vessel after deflating the balloon;
   reinflating the balloon after rotating the catheter; and
   reactivating the laser to ablate material within the vessel after reinflating the balloon.

9. The method of claim 8, wherein reactivating the laser to ablate material includes rotating the catheter within the vessel while the laser is reactivated.

10. The method of claim 8, wherein reactivating the laser includes advancing the catheter within the vessel while the laser is reactivated.

11. The method of claim 5, further comprising:
    deactivating the laser after inflating the balloon and activating the laser; and
    deflating the balloon after deactivating the laser;
    rotating the catheter within the vessel after deflating the balloon;
    reinflating the balloon after rotating the catheter; and
    reactivating the laser to ablate material within the vessel after reinflating the balloon.

12. The method of claim 1, wherein activating the laser to ablate material includes:
    activating the laser to ablate material within the vessel before inflating the balloon; and
    activating the laser to ablate material within the vessel after inflating the balloon.

13. The method of claim 12, wherein activating the laser to ablate material before inflating the balloon includes advancing the catheter within the vessel while the laser is activated, and activating the laser to ablate material after inflating the balloon includes advancing the catheter within the vessel while the laser is activated.

14. The method of claim 12, wherein activating the laser to ablate material after inflating the balloon includes rotating the catheter within the vessel while the laser is activated.

15. The method of claim 1, wherein the light guide comprises at least one optical fiber.

16. The method of claim 1, wherein the light guide comprises a liquid medium.

17. The method of claim 1, wherein inflating the balloon to adjust the distal end of the light guide includes engaging the light guide with the balloon to bias the light guide away from the central axis from the catheter body.

18. The method of claim 1, wherein the catheter further comprises a guidewire lumen, and positioning the catheter within the vessel includes sliding the catheter over a guidewire wherein the guidewire is received in the guidewire lumen.

19. The method of claim 18, wherein the catheter body includes a proximal guidewire port coupled with the guidewire lumen.

20. The method of claim 1, wherein the catheter further comprises a balloon lumen coupled with the balloon and extending within the catheter body, and inflating the balloon includes delivering a fluid to the balloon via the balloon lumen.

* * * * *